(12) United States Patent
Vandierendonck et al.

(10) Patent No.: US 12,343,490 B2
(45) Date of Patent: *Jul. 1, 2025

(54) MEDICINE DELIVERY AND ANIMAL MANAGEMENT SYSTEMS

(71) Applicant: JVD, INC., San Jose, CA (US)

(72) Inventors: Michael L. Vandierendonck, Scotts Valley, CA (US); Marcelo A. Martinez, Davis, CA (US)

(73) Assignee: JVD, INC., San Jose, CA (US)

(*) Notice: Subject to any disclaimer, the term of this patent is extended or adjusted under 35 U.S.C. 154(b) by 1043 days.

This patent is subject to a terminal disclaimer.

(21) Appl. No.: 17/331,730

(22) Filed: May 27, 2021

(65) Prior Publication Data

US 2021/0283386 A1 Sep. 16, 2021

Related U.S. Application Data

(63) Continuation of application No. 16/379,943, filed on Apr. 10, 2019, now Pat. No. 11,020,576.
(Continued)

(51) Int. Cl.
*A61M 31/00* (2006.01)
*A01K 11/00* (2006.01)
(Continued)

(52) U.S. Cl.
CPC ......... *A61M 31/002* (2013.01); *A01K 11/007* (2013.01); *A01K 11/008* (2013.01);
(Continued)

(58) Field of Classification Search
CPC ............ A61M 31/002; A61M 25/0127; A61M 2205/0272; A61M 2205/3344;
(Continued)

(56) References Cited

U.S. PATENT DOCUMENTS

| 3,659,600 A | 5/1972 | Merrill |
|---|---|---|
| 4,196,187 A | 4/1980 | Dannelly et al. |
| | (Continued) | |

FOREIGN PATENT DOCUMENTS

| DE | 10221484 A1 | 11/2003 |
|---|---|---|
| GB | 2455700 A | 6/2009 |
| WO | 2009144625 A1 | 12/2009 |

OTHER PUBLICATIONS

International Search Report and Written Opinion dated Feb. 2, 2017 for Application No. PCT/US2016/064026.
(Continued)

*Primary Examiner* — Theodore J Stigell
(74) *Attorney, Agent, or Firm* — Patterson + Sheridan, LLP

(57) ABSTRACT

Embodiments disclosed herein include devices for time release of measured quantities of an active ingredient and storage of animal management information. One embodiment disclosed herein releases an active ingredient, and then, at optionally varied intervals, releases additional doses into the same environment. The active ingredients are compartmentalized and, upon receiving an appropriate signal, open to dispense the active ingredient into the animal. Accordingly, in one embodiment, a device includes an engagement member to move a cap to dispense the active ingredient, and in another embodiment, includes a pellet that is attached to the cap to move the cap and dispense the active ingredient.

13 Claims, 18 Drawing Sheets

Related U.S. Application Data

(60) Provisional application No. 62/655,867, filed on Apr. 11, 2018.

(51) Int. Cl.
*A61D 7/00* (2006.01)
*A61M 25/01* (2006.01)

(52) U.S. Cl.
CPC .......... *A61D 7/00* (2013.01); *A61M 25/0127* (2013.01); *A61M 2205/0272* (2013.01); *A61M 2205/3344* (2013.01); *A61M 2205/52* (2013.01); *A61M 2205/8206* (2013.01); *A61M 2230/208* (2013.01); *A61M 2230/50* (2013.01); *A61M 2230/65* (2013.01); *A61M 2250/00* (2013.01)

(58) Field of Classification Search
CPC ...... A61M 2205/52; A61M 2205/8206; A61M 2230/208; A61M 2230/50; A61M 2230/65; A61M 2250/00; A01K 11/007; A01K 11/008; A61D 7/00
See application file for complete search history.

(56) References Cited

U.S. PATENT DOCUMENTS

| | | | |
|---|---|---|---|
| 4,425,117 A * | 1/1984 | Hugemann | ............. A61D 7/00 604/890.1 |
| 4,564,363 A | 1/1986 | Bagnall et al. | |
| 4,684,516 A | 8/1987 | Bhutani | |
| 5,217,449 A | 6/1993 | Yuda et al. | |
| 6,428,469 B1 | 8/2002 | Iddan et al. | |
| 7,048,730 B2 * | 5/2006 | Petrakis | ................... G01K 3/00 604/890.1 |
| 9,474,853 B2 | 10/2016 | Choy et al. | |
| 10,639,463 B2 | 5/2020 | Vandierendonck et al. | |
| 11,020,576 B2 * | 6/2021 | Vandierendonck | .. A01K 11/007 |
| 2001/0051766 A1 | 12/2001 | Gazdzinski | |
| 2003/0150832 A1 | 8/2003 | Bakhshaee et al. | |
| 2003/0187320 A1 | 10/2003 | Freyman | |
| 2005/0245902 A1 | 11/2005 | Cornish et al. | |
| 2006/0266370 A1 | 11/2006 | Tan | |
| 2007/0213659 A1 | 9/2007 | Trovato et al. | |
| 2007/0270630 A1 | 11/2007 | Houzego et al. | |
| 2008/0188837 A1 | 8/2008 | Belsky et al. | |
| 2009/0043278 A1 | 2/2009 | Tanaka et al. | |
| 2009/0182207 A1 | 7/2009 | Riskey et al. | |
| 2009/0281387 A1 | 11/2009 | Takizawa et al. | |
| 2009/0306473 A1 | 12/2009 | Tanaka et al. | |
| 2012/0071710 A1 * | 3/2012 | Gazdzinski | .............. A61B 8/12 600/101 |
| 2012/0089130 A1 | 4/2012 | Gyurik et al. | |
| 2012/0277550 A1 | 11/2012 | Rosenkranz et al. | |
| 2017/0151423 A1 | 6/2017 | Vandierendonck et al. | |

OTHER PUBLICATIONS

International Search Report and Written Opinion dated Jun. 21, 2019 for Application No. PCT/US2019/026703.

* cited by examiner

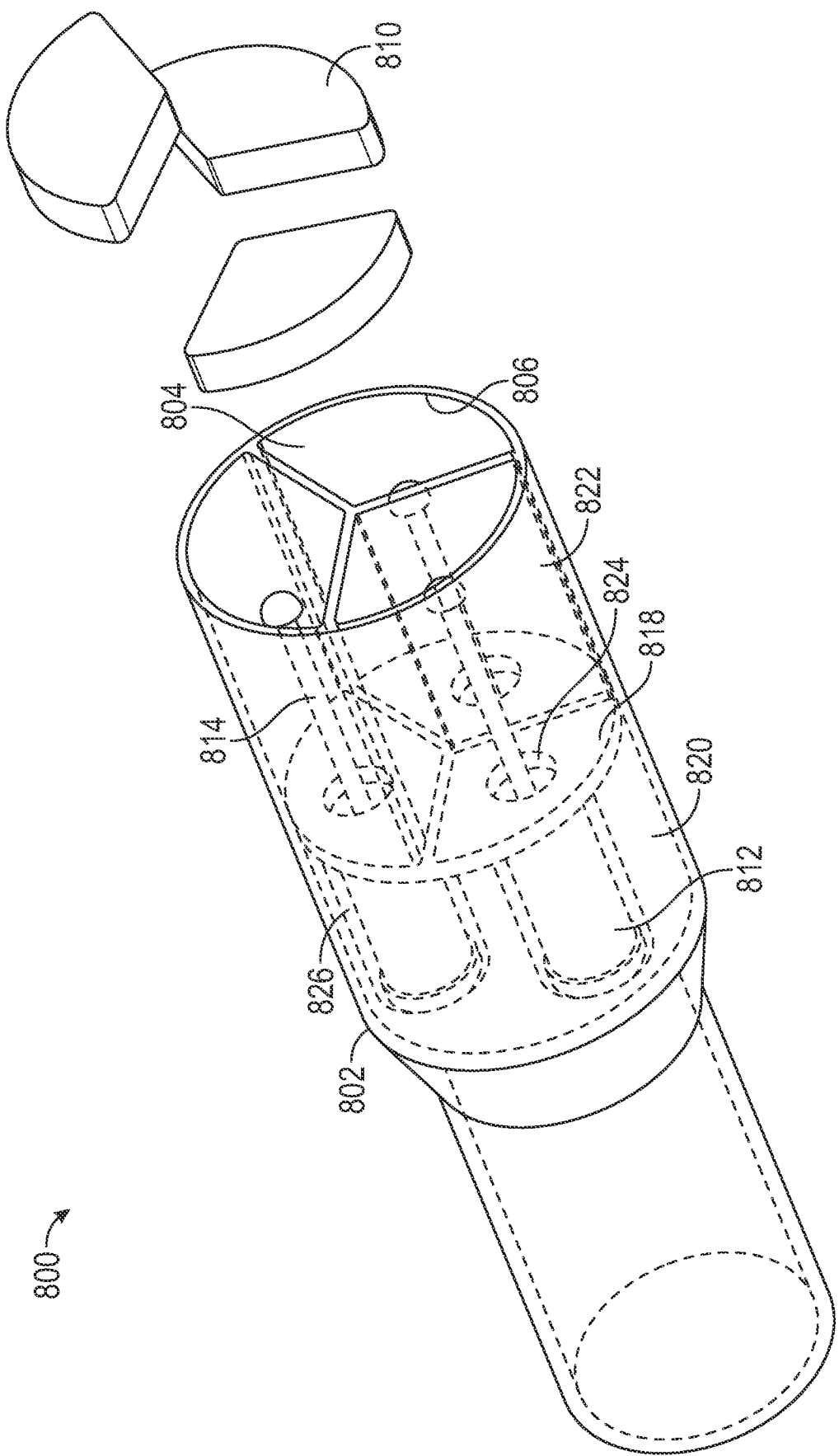

MEDICINE DELIVERY AND ANIMAL MANAGEMENT SYSTEMS

CROSS-REFERENCE TO RELATED APPLICATIONS

This application is a continuation application of U.S. patent application Ser. No. 16/379,943, filed Apr. 10, 2019, now U.S. Pat. No. 11,020,576, which claims benefit of U.S. Provisional Patent Application No. 62/655,867, filed Apr. 11, 2018, which are herein incorporated by reference in its entirety.

BACKGROUND

Field

Embodiments of the present disclosure generally relate to devices for controlled release of a supplement or a medicine and/or storage of animal management information.

Description of the Related Art

A large number of grazing species of animals, including cattle, sheep, goats and deer are classified as ruminant animals. Such animals possess four stomach compartments as part of their digestive system. These animals rely largely on the digestion of grass and other native vegetation for nutrients and sustenance. However, there are large tracts of grasslands throughout the world that are deficient in one or more of the mineral elements required by grazing animals.

A convenient way of supplying these animals with minerals, vitamins or other dietary or medicinal needs is by means of a bolus. A bolus is an object containing and releasing the required supplement or medicine at the required rate to improve or maintain the health of the animal. Such a device is administered to the animal by mouth and lodges naturally (by means of being sufficiently dense or by being fitted with tags or wings which deploy after administration) in either of the first two stomach compartments of the subject animal. Thereafter, the supplement or medicament is released over a period of time influenced by the size, shape and constituent ingredients of the bolus. Many different bolus designs have been utilized to satisfy the particular needs of animals, especially sheep and cattle under different grazing conditions.

The use of boluses in the treatment of ruminants is well known in the veterinary field. Such products are often weighted by a heavy density substance, such as iron or sand, in order to remain in the rumen to release a medicament. If sustained release coatings are present, the release is gradual until the source of medicine is exhausted.

However, such bolus designs are limited to sustained release and not time controlled release. Thus, the supplement or medicine is administered as required or at a generally constant rate over a limited period of time. Further, the use of multiple drugs simultaneously, which are not part of an approved combination, in a standard bolus would require significant testing and regulatory approval. As such, the creation of certain combination drugs would require immense cost and time for regulatory approval.

Additionally, the locations and other pertinent data of the ruminant animals need to be tracked and stored. Conventional ways of tracking these animals is with ear identification tags, RFID tags, or ruminal boluses. However, ear identification tags are only readable over a small range and require expensive readers, and RFID tags and ruminal boluses are expensive.

Thus, there is a need in the art for a supplement or medicine delivery system and an animal management information storage device which overcome the above described limitations.

SUMMARY

Embodiments disclosed herein include devices for delayed release of an active ingredient. In one embodiment, a delayed delivery device can include a device enclosure, the device enclosure having one or more device enclosure walls that are fluidly sealed; an ingredient enclosure positioned inside of the device enclosure, the ingredient enclosure having fluidly sealed walls and an opening, the ingredient enclosure fluidly sealed with the device enclosure walls to form a first chamber between the device enclosure and the ingredient enclosure; a cap positioned in the opening forming a second chamber, the second chamber having a pellet and an active ingredient positioned therein; an electronic control device disposed in the first chamber, the electronic control device comprising: a timer; a remotely operable activation switch in electrical connection with the timer; a power source; and a discharge device in connection with the power source; and a power coil positioned to deliver a magnetic field to the pellet, the power coil being electrically connected with the power source.

In another embodiment, a delayed delivery device can include an ingredient enclosure comprising one or more ingredient enclosure walls, the ingredient enclosure walls being fluidly sealed, the ingredient enclosure walls forming an interior region and a delivery opening; a ferromagnetic pellet positioned in the interior region; a cap for fluidly sealing the delivery opening; a device enclosure comprising one or more device enclosure walls, the device enclosure walls forming a sealed exterior region around at least a portion of the ingredient enclosure; a weight connected with the device enclosure, the weight being sufficient to retain the delayed delivery device in a rumen; an electronic control device disposed in the sealed exterior region, the electronic control device comprising: a timer; a remotely operable activation switch in electrical connection with the timer; a power source; and a discharge device in connection with the power source; and a power coil disposed around a portion of the ingredient enclosure, the power coil being electrically connected with the power source.

In another embodiment, a delayed delivery device can include an ingredient enclosure comprising one or more ingredient enclosure walls, the ingredient enclosure walls being fluidly sealed, the ingredient enclosure walls forming an interior region and a delivery opening; an active ingredient in a dispersible form within the interior region; a ferromagnetic pellet positioned in the interior region at a position distal from the delivery opening, such that the active ingredient is between the ferromagnetic pellet and the delivery opening; a cap fluidly sealing the delivery opening; a device enclosure comprising one or more device enclosure walls, the device enclosure walls forming a sealed exterior region around at least a portion of the ingredient enclosure; a weight connected with the device enclosure, the weight being sufficient to retain the delayed delivery device in a rumen and interspersed within the active ingredient; an electronic control device disposed in the device enclosure, the electronic control device comprising: a timer; a remotely operable magnetic switch in electrical connection with the timer; a power source comprising a battery and a capacitor; and a discharge device in connection with the power source; a launch tube positioned distal from the delivery opening; and a power coil disposed around the launch tube, the power coil being electrically connected with the power source through the discharge device.

In another embodiment, an animal management device is disclosed. The animal management device includes a base portion and a cap defining an interior region, and an electronics portion at least partially disposed in the interior region. The electronics portion may include a short range transceiver for sending and receiving management information of an animal, a computer processing unit having memory for storing the management information of the animal, and an antenna. The base portion may comprise more than fifty percent of a length of the animal management device. The cap and the base portion defining an interior region for housing the electronics portion.

In another embodiment, a method for animal management is disclosed. The method may include programming an animal management device to store animal management information, inserting the animal management device into an animal, and transmitting a request to the animal management device for the stored animal management information.

In another embodiment, a delayed ingredient device is disclosed. The delayed ingredient delivery device includes an enclosure defining an interior region and a delivery opening; a cap removably inserted into the delivery opening to seal the delivery opening; a pellet comprising a ferromagnetic material and movably positioned in the interior region; an engagement member positioned between the pellet and the cap to move and engage the cap when the pellet moves in the interior region; an electronic control device comprising a power source; and a power coil electrically connected with the power source to generate a magnetic field and move the pellet in the interior region.

In another embodiment, a delayed ingredient device is disclosed. The delayed ingredient delivery device includes an enclosure defining an interior region and a delivery opening; a cap removably inserted into the delivery opening to seal the delivery opening; a pellet comprising a ferromagnetic material connected to the cap and movably positioned in the interior region; an electronic control device comprising a power source; and a power coil electrically connected with the power source to generate a magnetic field and move the pellet in the interior region.

In yet another embodiment, a delayed ingredient device is disclosed. The delayed ingredient delivery device includes an enclosure defining an interior region and a delivery opening; a cap removably inserted into the delivery opening to seal the delivery opening; a base plate comprising an aperture and positioned in the interior region to define a pellet chamber and an ingredient chamber; a pellet movably positioned in the pellet chamber; and an engagement member positioned between the pellet and the cap that extends through the aperture to move and engage the cap when the pellet moves in the pellet chamber.

BRIEF DESCRIPTION OF THE DRAWINGS

So that the manner in which the above recited features of the present disclosure can be understood in detail, a more particular description of the disclosure, briefly summarized above, may be had by reference to implementations, some of which are illustrated in the appended drawings. It is to be noted, however, that the appended drawings illustrate only typical implementations of this disclosure and are therefore not to be considered limiting of its scope, for the disclosure may admit to other equally effective implementations.

FIGS. 8A-8D are side views depicting a delayed delivery device, according to embodiments described herein.

To facilitate understanding, identical reference numerals have been used, wherever possible, to designate identical elements that are common to the Figures. Additionally, elements of one implementation may be advantageously adapted for utilization in other implementations described herein.

DETAILED DESCRIPTION

Embodiments disclosed herein include devices for releasing measured quantities of an active ingredient. One embodiment described herein releases an active ingredient, which is useful in the ruminant art, within a rumen or other portions of the gastrointestinal tract and, then, at optionally varied intervals, releases additional doses into the same environment. The active ingredients are compartmentalized and, upon receiving an appropriate signal, are expelled into the rumen of the animal. The doses of active ingredient may be delivered simultaneously, sequentially, or independently. Further, the doses of active ingredient may be the same active ingredient or different active ingredients, in any formulation.

The release regimen for an active ingredient using the embodiments described herein, therefore, comprises the release of a single dosage unit or a series of dosage units of the active ingredient. The dosage units are released in timed increments rather than in a sustained release pattern. This allows an effective treatment to be spread over a longer time span per space of dosage unit than many of the prior art sustained release products. Further, this timed release design allows for a full dose to be received at a specific time, rather than as accumulated over a time period, as seen in a sustained release pattern. Embodiments disclosed herein are more clearly described with reference to the figures below.

Figure 1:
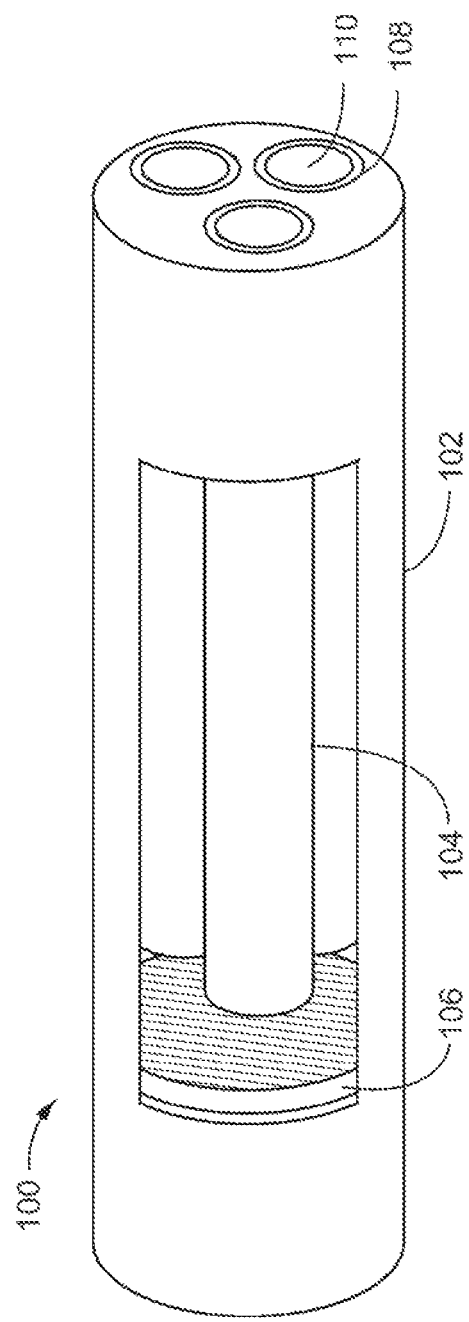
FIG. 1 is a side perspective view of a delayed delivery device, according to embodiments described herein.

FIG. 1 is a side perspective view of a delayed delivery device 100, according to embodiments described herein. The delayed delivery device 100 comprises a device enclosure 102 and a plurality of ingredient enclosures 104. The device enclosure 102 and the ingredient disclosures 104 are depicted as cylindrical, but may be of other shapes, as desired by the operator. The device enclosure 102 contains the ingredient enclosure 104 and an electronic control device 106.

The device enclosure 102 can be one or more device enclosure walls of non-biodegradable composition. The device enclosure 102 can be any shape suitable for pharmaceutical delivery. In one example, the device enclosure 102 is formed in a capsular or cylindrical shape. The device enclosure 102 can have one or more openings 108. The one or more openings 108 form a water tight seal. In one example, the one or more opening 108 form a water tight seal in connection with a portion of the ingredient enclosures 104. Further, the one or more openings 108 can correspond to the number of ingredient enclosures 104.

The ingredient enclosures 104 can also be a non-biodegradable composition. The ingredient enclosures 104 may be formed in a cylindrical shape, each having an opening 110. The opening 110 is closed with a removable water tight cap 216, such as a diaphragm, plug, cap or cover. The ingredient enclosure 104 and the caps 216 are described below with reference to FIG. 2A.

The outer dimensions of each delayed release assembly are, for example, from 100 mm to 200 mm in length, 20 mm to 50 mm in diameter with about a 1 mm to 3 mm wall thickness. In one example, the overall size will be about 30 mm diameter and about 125 mm in length. A whole bolus for ruminant application will be from about 50 mm to 150 mm in length by about 25 mm to 75 mm in diameter. The size of the product form is dictated by the number of doses, the dose volume, and the application for which the delayed release of an active ingredient is to be used. The above embodiments are exemplary and not intended to be limiting of possible sizes.

The device enclosure 102 and the ingredient enclosures 104 can include or be composed of a high molecular weight polyethylene or polypropylene polymer. Also, a silicone elastomer may be used. Alternative wall materials are soft polystyrene, polycarbonate, polyvinylchloride, polysulfone, polymethylpentene, polyimide polymers or combinations thereof. Non-organic materials include a corrosion resistant metal such as stainless steel, a ceramic or a non-friable glass. The term "non-biodegradable" is used to indicate that the wall material is resistant to its target milieu, for example the rumen environment, over the desired time of ingredient release.

The electronic control device 106 is positioned in the device enclosure 102. The electronic control device 106 comprises one or more components that can receive an external signal, initiate a timer and deliver a timed magnetic pulse. The timed magnetic pulse may be automatic. The composition, operation and use of the electronic control device 106 are described in more detail with reference to FIG. 2B.

Figure 2A:
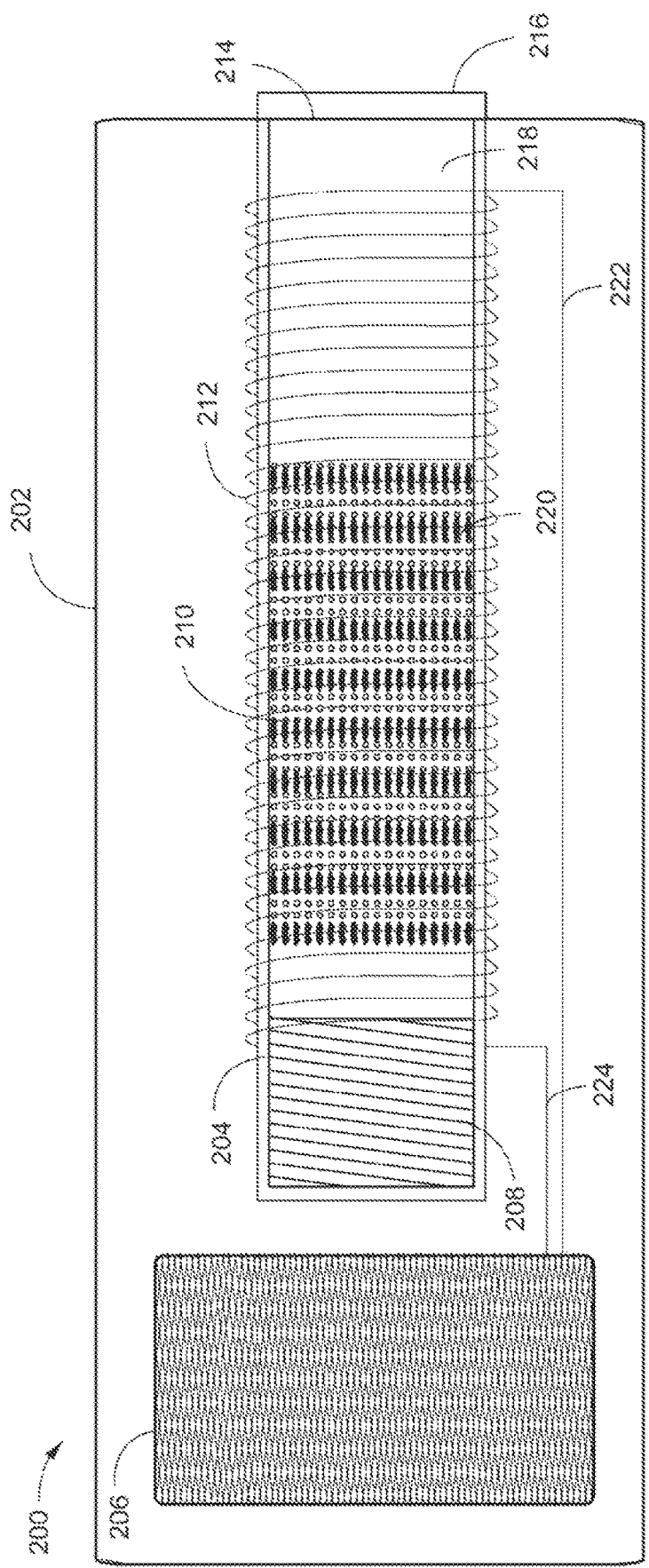
FIG. 2A is side view of a delayed delivery device, according to embodiments described herein.

FIG. 2A is a side view of a delayed delivery device 200, according to embodiments described herein. The delayed delivery device 200 includes a device enclosure 202 and an ingredient enclosure 204. The device enclosure 202 contains the ingredient enclosure 204 and an electronic control device 206. The ingredient enclosure 204 contains a pellet 208 and a medicament 210. A power coil 212 is disposed around at least a portion of the ingredient enclosure 204. The ingredient enclosure 204 further has a delivery opening 214. The delivery opening is sealed by a cap 216.

The device enclosure 202 forms a water tight barrier around the components of the delayed delivery device 200, including at least a portion of the ingredient enclosure 204, the power coil 212 and the electronic control device 206. The device enclosure 202 can be substantially similar to the device enclosure 102, as described with reference to FIG. 1.

The ingredient enclosure 204 can have a shape and composition substantially similar to the ingredient enclosure 104 described with reference to FIG. 1. The ingredient enclosure 204 can be water tight, with the exception of the opening 214. The seal between the device enclosure 202 and the ingredient enclosure 204 maintains the opening of the ingredient enclosure 204 for receiving the cap 216, while closing off the interior of the device enclosure 202. The seal between the device enclosure 202 and the ingredient enclosure 204 may be a gasket style seal or a permanent seal. The ingredient enclosure 204 includes a compartment for the storage of the medicament 210 and a cap 216 positioned to seal the opening 214.

Figure 4A:
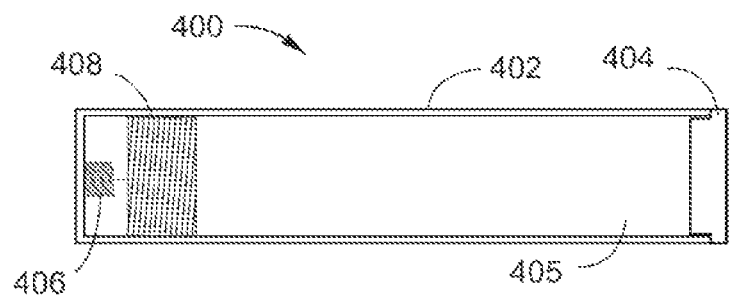
FIGS. 4A-4D are side views of ingredient enclosures, according to embodiments described herein.
Figure 4B:
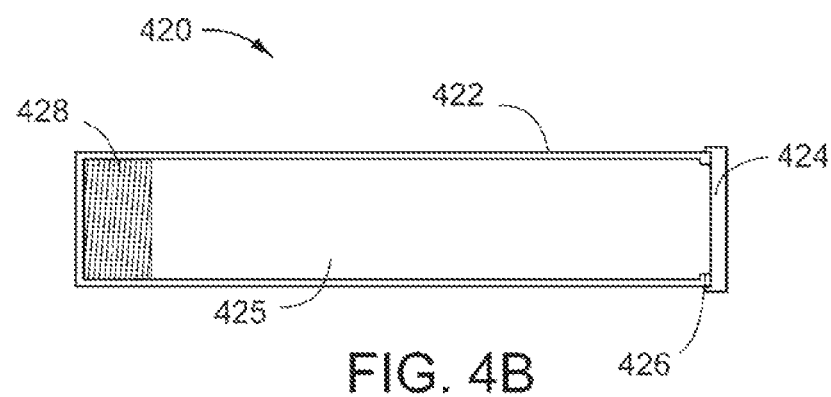

The ingredient enclosure 204 can be made of the same material as that used for the device enclosure 202. The combination of the ingredient enclosure 204 and the cap 216 create a sealed chamber 218. The cap 216 can be easily removed by internal pressure, such as the pressure of the medicament 210 against the cap 216. The cap 216 may be positioned in connection with the opening 214 using adhesives, grooves to snap into place or other methods/devices for sealably connecting the cap. In one embodiment, the cap 216 is a diaphragm, which may be held in place with adhesive or light crimping. At times, the cap 216 may have a lower durometer or hardness reading than that of the material used for the ingredient enclosure 204. In another embodiment, the cap 216 is a simple cylindrical plug which is kept in place by external liquid pressure and adhesion to the ingredient enclosure 204. An internally arranged closure is illustrated in FIG. 4A; an externally arranged closure is illustrated in FIG. 4B.

The pellet 208 is positioned in the ingredient enclosure 204. The pellet 208 includes a ferromagnetic material, such as iron (Fe), nickel (Ni), cobalt (Co) and alloys thereof. The pellet 208 is shown as a cylinder which acts as a plunger to expel medicament. Other shapes which provide the same function are also contemplated, e.g., spheroid, rectangular or other shapes depending on the shape of the ingredient enclosure 204 and function desired. The pellet 208 may further include a protective coating. Protective coatings can include polymers, inert compounds or others which would prevent digestion of the pellet 208.

The pellet 208 is shown positioned in the ingredient enclosure 204 at the opposite end from the opening 214. The medicament 210 is positioned between the pellet 208 and the opening 214. When the pellet 208 receives a magnetic field, the pellet 208 is moved from the opposite end of the ingredient enclosure 204 to the opening 214. However, other positions may be used, such as the pellet 208 positioned in the center of the ingredient enclosure 204. In this embodiment, the pellet 208 may be surrounded by the medicament 210. In further embodiments, the ingredient enclosure 204 may include components for relief of back vacuum, such as a relief hole formed in the pellet 208, a pressurized ingredient enclosure 204 or other components such that any vacuum created by expelling the medicament 210 or by moving the pellet 208 does not prevent the delivery of the medicament 210.

The medicament 210 comprises one or more active ingredients which are combined with optional dispersants, disintegrators, fillers, granulation agents or lubricants as discussed above. If the active ingredient has limited water solubility, the particle size of the active ingredient is sized so that the medicament 210 will be expelled forcefully through the vacated opening of the assembly into the target area. The medicament 210 may be in the form of a liquid, powder, slug, granule, sustained release granule or mini-bolus and may be either readily soluble or easily dispersible by the use of various pharmaceutical aids.

Any medicament or growth promotant which an operator desires to administer to ruminants such as cattle, sheep or goats in a discrete number of doses over a period of time are suitable active ingredients for administration using embodiments described herein. A non-exhaustive list of possible active ingredients includes anthelmintics such as albendazole, fenbendazole, oxfendazole, ivermectin, thiabendazole, mebendazole, cambendazole, pyrantel, morantel or levamisole; antibiotics such as streptomycin, virginiamycin, a vancomycin-like glycopeptide, a tetracycline, any of the penicillin or cephalosporin class or an ionophore; sulfa drugs especially sulfamethazine; trace metals necessary for metabolism such as selenium, copper, zinc or cobalt; vitamins; hormones or oral vaccines useful in the veterinary field. It will be understood by one skilled in the art that the active ingredient, if not readily water soluble, can be prepared in a readily dispersed form prepared as known to the art and as described herein.

A typical dispersive medicament preparation in the form of a dosage unit, which is useful for charging an active ingredient chamber of a ruminant device, comprises finely divided albendazole (1.92 g), polyoxyethylene(20)sorbitan monooleate (0.06 g) and "Centrophase C" (0.2 g and which is lecithin plus a wetting agent). Another composition contains albendazole powder 70.0% w/w, magnesium stearate 1.0%, starch 8.0% and dicalcium phosphate dihydrate, 21%. One of either of these dosage units can be charged into each chamber of a three-chambered unit, described herein, which is set to be released at 10 minutes, 30 days and 60 days or any other time interval. The bolus unit is then administered to cattle which are infected, or liable to infection, with nematodes.

This aspect of the embodiments can achieve a repeat action of the medicament by periodic release of dosage units in the rumeno-reticular sac of ruminants rather than a sustained release of medicament as known to the art.

Pharmaceutical aids include pharmaceutical fillers such as kaolin, mannitol, a powdered or granulated sugar, dicalcium phosphate, starch, microcrystalline cellulose, lactose or calcium phosphate; binders such as gelatin, gums or sugars; lubricants such as a metal stearate, a fatty acid, talc, graphite or cocoa butter; or granulating agents such as zein, acacia, tragacanth, gelatin, sodium alginate, a cellulosic derivative or magnesium stearate.

Disintegrators or wicking agents, which are used in the pharmaceutical art for granulations or tablets, are particularly useful for insuring that the active ingredient will be expelled from either an initial or a delayed release compartment, the latter after a cap 308 of the delayed delivery device 304 is displaced by an internal removal means. Such compounds include potato starch, cornstarch, "Veegum HV", methylcellulose, agar, bentonite, sponge material, cation-exchange resins, alginic acid, guar gum, citrus pulp, carboxymethylcellulose and, especially, sodium starch glycolate. Other agents, such as carbon dioxide generating agents, for example sodium bicarbonate-citric acid, may also be used. The disintegrator can be present in from about 2% to about 10% by weight of formulation which contains the active ingredient.

The delayed delivery device 200 may further comprise a weight 220 to hold the delayed delivery device 200 in position prior to medicament delivery. Weight 220 may comprise materials such as sand, bentonite, iron pellets or filings, glass pellets, heavy metal salts such as calcium sulfate dihydrate, cementitious matter or clay balls, which may be optionally used when the weight 220 may be either incorporated into a wall of any component of the delayed delivery device 200 or distributed with the medicament 210. The weight 220 should be sufficient to enable the delayed delivery device 200 to remain in the rumen sack throughout the treatment period by itself or as part of the complete bolus which has already released earlier units of active ingredient. The entire unit or each delayed action assembly, as the case may be in ruminants, will have a density which is sufficient to retain the delayed delivery device 200 in the rumen until the period of drug delivery is complete. The weight 220 is not an essential part of the assembly for all applications as the medicament and other components may provide sufficient weight to retain the assembly during the course of treatment.

A power coil 212 is disposed around at least a portion of the ingredient enclosure 204. The power coil 212 comprises a conductive material capable of generating an electromagnetic field in the ingredient enclosure 204. The electromagnetic field is used to move the pellet 208 within the ingredient enclosure 204 to expel the medicament in the ingredient enclosure 204. The power coil 212 may include a metal, such as copper, aluminum, gold, silver, other metals or combinations. The power coil 212 can be formed by a wire that is wound in a spiral on the ingredient enclosure 204 surface. In another embodiment, the power coil 212 can be formed by a thin layer of electrically conductive material that has been etched to form the spiral pattern. Electrical wires 222 and 224 are connected to the ends of the power coil 212, respectively.

Figure 2B:
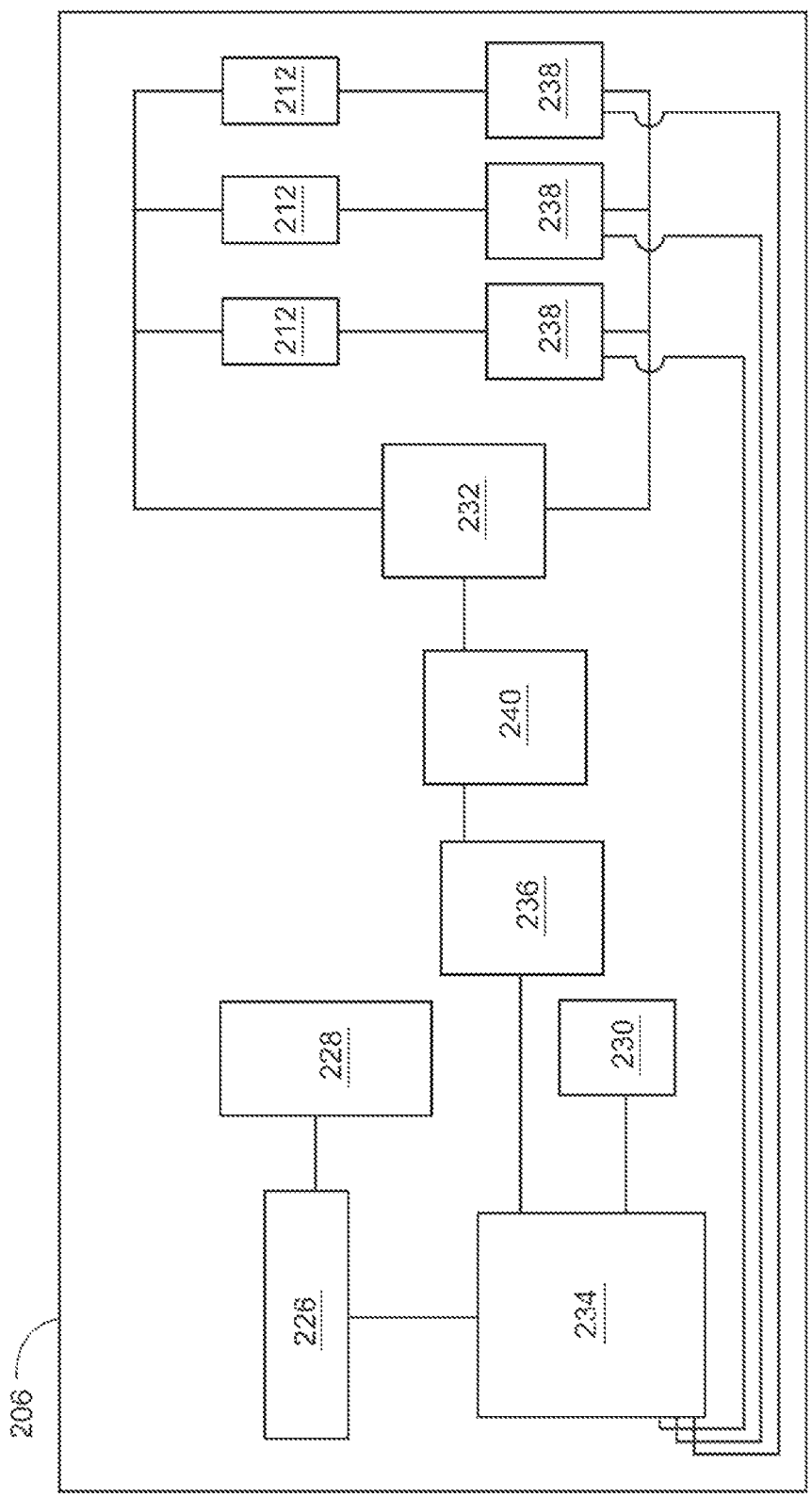
FIG. 2B is a schematic diagram of the electronic control device, according to embodiments described herein.

FIG. 2B is a schematic diagram of the electronic control device 206, according to embodiments described herein. The electronic control device 206 is positioned within the device enclosure 202, such that the electrical wires 222 and 224 can be electrically connected to the electronic control device 206. The electronic control device 206 comprises one or more components for control of operation and timing for the delayed delivery device 200. Upon receiving a signal from an external source and on further timing input, the electronic control device 206 is configured to charge and discharge a capacitor 232 such that a short magnetic field is created in the inner region of the power coils 212, the magnetic field moving the pellet 208.

The components can include a remote switch 226, controlling an electrical connection between a battery 228 and a logic controller 234. The logic controller 234 can be electrically connected or controlling an electrical connection with a timer 230, a charge oscillator 236, a capacitor 232 and at least one discharge device 238. The logic controller 234 is connected such that the logic controller 234 can activate and deactivate the discharge from the capacitor 232. The capacitor 232 is connected through the discharge devices 238 to a power coil 212.

The remote switch 226 is a switch that can be activated remotely. In one embodiment, the remote switch 226 is an electrical switch activated or operated by an applied magnetic field, such as a reed switch. The remote switch 226 may further include an electrical switch activated or operated through radio waves, such as a Bluetooth connection, a Wi-Fi connection or others. The remote switch 226 is positioned between the battery 228 and one or more other devices, such that the battery 228 is not drained while waiting for a signal.

When the remote switch 226 is activated, the remote switch 226 connects the battery 228 to the logic controller 234. The logic controller 234 controls the charging and the discharge of the capacitor 232 as well as generating the timing signals, in conjunction with the timer 230, for the programmed delivery of the active ingredient. The logic controller 234 can be programmed such that specific enclosures can be opened based on time intervals received from a timer 230. The ingredient enclosure 204 affected and the time interval for the specific ingredient enclosure 204 can be programmed into the logic controller 234 either prior to administration of the delayed delivery device 200 or after administration.

With the remote switch 226 active, the battery 228 provides electrical current to the electronic control device 206. The battery 228 may be a power source suitable for long term storage at body temperature, such as a lithium ion battery. The battery 228 may be a chemical battery, a solid state battery or others capable of storing sufficient power for the life of the delayed delivery device 200.

Once power is received from the battery 228, the control logic of the logic controller 234 activates the timer 230. The timer 230 is configured to provide information on one or more timing intervals to the logic controller 234. The timer 230 holds one or more time-based set points for activation of the delayed delivery device 200. Possible timers which can be adapted for use as the timer 230 include analog clocks, digital clocks, delayed switches or other devices which can provide activation information after a known period of time. In one embodiment, the timer 230 comprises a single chip microcontroller which is essentially a microcomputer containing system timing, internal logic, ROM and input/output necessary to implement the dedicated control functions to initiate the timing periods and then measure the time periods and direct sufficient energy from the battery 228 to the charge control 234 to trigger the charging and discharging of the power coil 212. The timing interval, for example, may be 10 minutes, 2 weeks, 4 weeks and 6 weeks or longer.

Once a designated period of time has passed, the timer 230 sends a signal to the logic controller 234. The logic controller 234, based on timing and other parameters of the control logic, then directs power to the charge oscillator 236. The charge oscillator 236 converts the power, delivered as a DC current from the battery 228, to an AC current. The AC current is delivered to the step up transformer 240 to increase voltage. Ending voltage resulting from the step up transformer should be at least 100 V, such as 200 V.

Though the remote switch 226 is described here as being remotely activated, further interactions with a remote signal may be used in an activation scheme by the remote switch 226. For example, the remote switch 226 may temporarily deactivate the delayed delivery device 200, where the delayed delivery device 200 is active. The delayed delivery device 200 may include a timer 230 which is in an active state and counting is counting down to a specific time point. The delayed delivery device 200 may be activated by ingestion, by environmental conditions (such as acidity or temperature), or combinations thereof. In this embodiment, the remote signal received at the remote switch 206 could cause a delay in the timer activation, turn on or off specific components of the electronic control device 206 or other control schemes.

The capacitor 232 receives and accumulates a charge at a point of time after the remote switch 226 is activated, such that the power coil 212 can be activated. The capacitor 232 is connected with the battery 228, through the charge control 234. The capacitor 232 is capable of holding a charge at a voltage above 100V, such as a voltage of between 100V and 500V. The current spike delivered from the capacitor 232 to the power coils 212 can be between 100 A and 500 A, such as 200 A.

Once the capacitor 232 is charged, the capacitor 232 can deliver the charge to one or more of the discharge devices 238. The discharge devices 238 are device which control the delivery of electrical power to a respective power coil 212. The discharge device 238 can be a thyristor, shown here as a silicon-controlled rectifier (SCR) device. A discharge device 238 receives a turn on voltage from the logic controller 234 at the designated time interval in the control logic. The voltage received closes the circuit, allowing power to flow from the capacitor and through the designated power coil 212. The flow through the power coil 212 creates a magnetic field in the ingredient enclosure 204.

In one embodiment of operation, delayed delivery device 200 is ingested by the animal or otherwise positioned in the rumen. Once in the rumen and after a prescribed time period, a user provides an activation signal. The activation signal, as described above can be in the form of a magnetic field, radio waves or others. Radio waves can include a Bluetooth connection, a Wi-Fi connection or others. The electronic control device 206 receives the input signals from the remote switch 226. The remote switch 226 then closes the circuit, thus activating the timer 230. The timer 230, after a designated amount of time, sends a signal to the charge control 234. The charge control 234 directs charge from the battery 228 to the capacitor 232 to charge the capacitor. The voltage of the charge from the battery 228 can be increased through the use of a step up transformer. Once charged, the capacitor 232 can then be discharged through charge control 234. The discharged electricity is delivered through electrical wires 222 and 224 to the power coil 212. The electric current through the power coil 212 generates a magnetic field that propels the pellet 208 at a high rate of speed toward the opening 214. The medicament 210 is pushed by the pellet 208 towards the opening 214 and the cap 216. The force from the pellet 208 and the medicament 210 creates a pressure on the cap 216, thus forcing the cap 216 away from the opening 214 and expelling the medicament 210 into the rumen.

Though the delayed delivery device 200 is primarily described as a medium for medicament delivery, the delayed delivery device 200 can alternatively provide one or more secondary functions. In one embodiment, the power coil 212 may be used as a magnetic antenna for communicating with the external source. As discussed below with FIG. 6, the delayed delivery device 200 may further include an electronic ID tag, such that the ruminant may be tracked. The delayed delivery device 200 may further be designed to receive remote delivery timing programming, such as over Wi-Fi or Bluetooth. Remote delivery of timing programming allows for changes in the dosage delivery scheme, after activation of the delayed delivery device 200 and inside of the ruminant animal. Further, remote delivery of timing programming would allow changes to be delivered, from any location, without physical manipulation of the delayed delivery device 200.

Thus, using the delayed delivery device 200, an active ingredient can be delivered to the rumen of a ruminant in a time delayed fashion. The user has primary control of the activation of the delayed delivery device 200 through the electronic control device 206. Multiple doses can be delivered in different time frames or immediately upon receipt of an activation signal, thus allowing for control of both dose size and timing. Further, multiple different active ingredients can be delivered in a controlled fashion as above. Finally, the use of magnetic fields allows the ingredient enclosure to be completely sealed, thus reducing costs and increasing reliability.

Figure 3A:
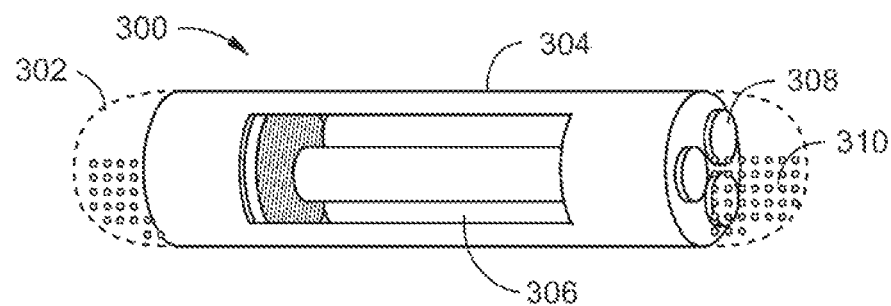
FIGS. 3A-3C are side perspective views depicting a capsule unit, according to embodiments described herein.
Figure 3B:
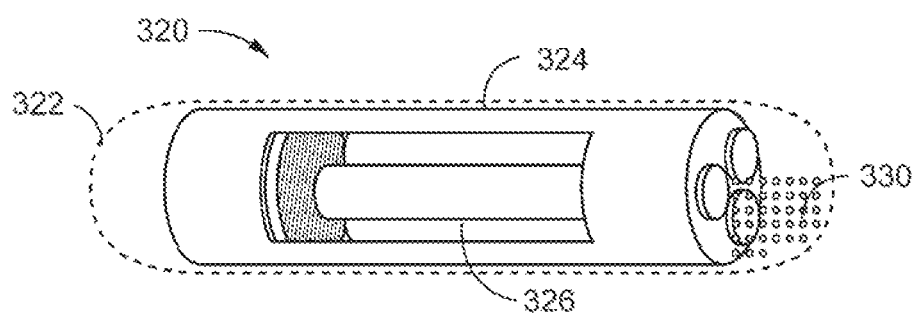
Figure 3C:
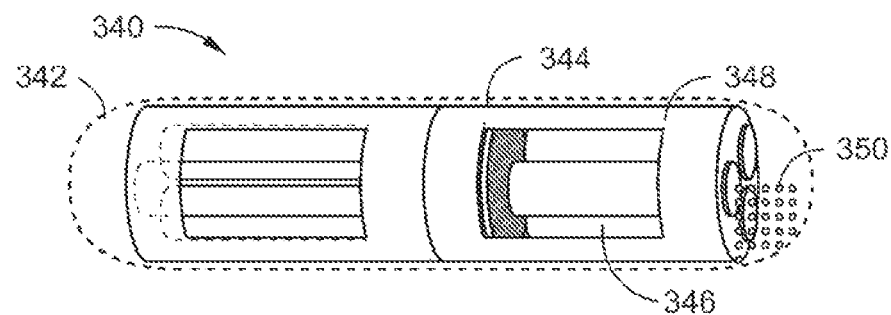

FIGS. 3A-3C are side perspective views depicting a capsule unit, according to embodiments described herein. The capsule units provide a safe means for oral delivery of the delayed delivery device, such that the ruminant is not injured by the device. Further, the capsule unit provides an extra layer of protection to prevent premature activation of the delayed delivery device, such as by physical perturbation during mastication or swallowing.

FIG. 3A depicts a capsule unit 300 having end covers 302 formed onto a delayed delivery device 304, according to one embodiment. The delayed delivery device 304 can be substantially as described with relation to FIGS. 1 and 2. As shown here, the delayed delivery device 304 includes three ingredient enclosures 306. The ingredient enclosures 306 may be substantially as described in FIGS. 1, 2 and as will further be described in FIGS. 4A-4E.

The end covers 302 may be composed of a biodegradable material, such as a biodegradable polymeric material, which is known to the pharmaceutical art, such as hard gelatin, soft gelatin or water soluble cellulosic derivatives such as methylcellulose, ethylcellulose or sodium carboxymethylcellulose. The term "biodegradable", as used herein, means a material which is either soluble in the rumen or otherwise readily disrupted by rumen content so the immediate dosage unit and delayed action assemblies are released.

The end covers 302 may contain a medicament 310 including an active ingredient which is available for initial release. Another dosage unit is located in the delayed delivery device 304 for timed release of a second unit of the active ingredient. The active ingredient may be in a form such that the delivery of the medicament 310 occurs immediately (e.g., the entire quantity of active ingredient in the medicament 310 is available at the time of release from the end covers 302) or over a period of time (e.g., the active ingredient in the medicament 310 is released over a period of time from the end covers 302, such as by dispersion of the medicament 310 in a biodegradable substance). The active ingredient in each of the end covers 302 or delayed delivery device 304 may be in powder, granule or slug form and may be either readily soluble or easily dispersible by the use of various pharmaceutical aids, as described above.

Once the end covers 302 have dissolved or otherwise been removed, the delayed delivery device 304 can then be activated as described above to release a medicament, according to embodiments described herein.

FIG. 3B depicts a capsule unit 320 having a capsule coating 322 positioned over a delayed delivery device 324, according to one embodiment. The delayed delivery device 324 can be substantially as described with relation to FIGS. 1 and 2. As shown here, the delayed delivery device 324 includes three ingredient enclosures 326. The ingredient enclosures 326 may be substantially as described in FIGS. 1, 2 and as will further be described in FIGS. 4A-4E.

The capsule coating 322 may have substantially the same composition as the end covers 302, described with reference to FIG. 3A. The capsule coating 322 may further include a medicament 330 having an active ingredient, as described with reference to FIG. 3A. The medicament 330 can completely surround the delayed delivery device 324 or just a portion thereof. As described above, as the capsule coating 322 dissolves, a first dose of active ingredient can be delivered through medicament 330. The delayed delivery device 324 can then be activated as described above to release a medicament, according to embodiments described herein.

FIG. 3C depicts a capsule unit 340 having a capsule coating 342 positioned over a delayed delivery device 344, according to one embodiment. The delayed delivery device 344 can be substantially as described with relation to FIGS. 1 and 2. As shown here, the delayed delivery device 344 includes six ingredient enclosures 346. The ingredient enclosures 346 may be substantially as described in FIGS. 1, 2 and as will further be described in FIGS. 4A-4E.

The capsule coating 342 may have substantially the same composition as the end covers 302, described with reference to FIG. 3A. The capsule coating 342 may further include a medicament 350 having an active ingredient, as described with reference to FIG. 3A. The medicament 350 can completely surround the delayed delivery device 344 or surround just a portion thereof. As described above, as the capsule coating 342 dissolves, a first dose of active ingredient can be delivered through medicament 350.

The delayed delivery device 344 can be activated as described above to release a medicament, according to embodiments described herein. In this embodiment, the openings of the ingredient enclosures are directed to both ends of the device enclosure 348 of the delayed delivery device 344. As such, delayed delivery devices, such as delayed delivery device 344, may include more ingredient enclosures 346 that are smaller and hence contain smaller doses of active ingredient. However, since there are more ingredient enclosures 346 more types of medicament can be delivered, more control of dosage can be achieved or combinations thereof.

FIGS. 4A-4D are side views of exemplary ingredient enclosures contemplated herein. The ingredient enclosures can be modified to provide further benefits, such as handling different formulations of active ingredients, controlling retention of the pellet or for other benefits as described below.

FIG. 4A depicts an ingredient enclosure 400 having a tether 406, according to one embodiment. As shown here, the ingredient enclosure 400 includes a wall 402 and a cap 404, creating a chamber 405. A pellet 408 is disposed in the chamber 405 and is attached to the tether 406. The ingredient enclosure 400 may have substantially the same shape and composition as the ingredient enclosure 204, described with reference to FIG. 2A. The power coil, such as power coil 212 described with reference to FIG. 2A, is present in this embodiment but is not shown here for clarity.

The tether 406 can be a string, a spring or other restraint such that the pellet 408 is bound to the chamber 405. The tether 406 can be made from a non-biodegradable composition, such as a metal or a polymer. The pellet 408 is accelerated from an origination point to the opening of the chamber 405, using the magnetic force of the power coil, as described previously. The pellet expels the medicament by forcing the medicament into contact with the cap 404, thus displacing the cap. Once the pellet 408 reaches a critical distance from its origination point, the tether 406 can either prevent further movement or retract the pellet 408 to a previous position, preventing the pellet 408 from entering the rumen.

The cap 404, shown here, is an internally arranged cap. Thus, a portion of the cap 404 is positioned inside of the chamber 405 and through friction, forms a water tight seal. The cap 404 may further include one or more components to assist in forming the desired friction level and maintaining a water tight seal, such as a gasket (not shown).

FIG. 4B depicts an ingredient enclosure 420 having a lip 426, according to one embodiment. As shown here, the ingredient enclosure 420 includes a wall 422 and a cap 424, creating a chamber 425. A pellet 428 is disposed in the chamber 425. The ingredient enclosure 420 may have substantially the same shape and composition as the ingredient enclosure 204, described with reference to FIG. 2A. The power coil, such as power coil 212 described with reference to FIG. 2A, is present in this embodiment but is not shown here for clarity.

The lip 426 formed at the opening extending into the inner diameter a sufficient distance to prevent the plug from moving past the lip on activation. The lip 426 may be continuous or discontinuous around the ID of the chamber. The lip may have the same composition as the wall 422. The pellet 428 is accelerated from an origination point to the opening of the chamber 425, using the magnetic force of the power coil, as described previously. The pellet 428 can then expel the medicament. Once the pellet 428 reaches the end of the chamber 425, the lip 426 prevents the pellet 428 from entering the rumen.

Figure 4C:
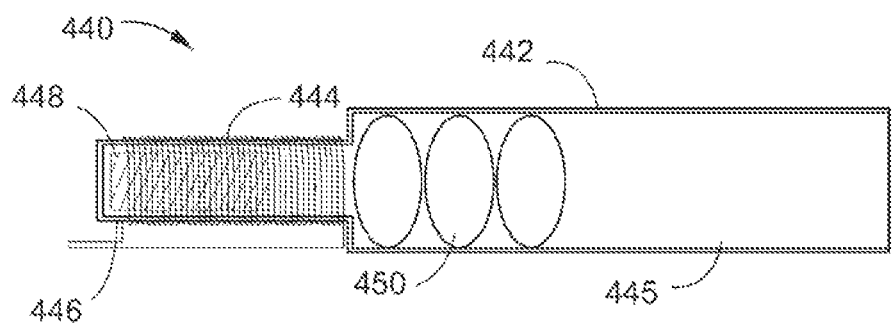

FIG. 4C depicts an ingredient enclosure 440 having a launch tube 446, according to one embodiment. As shown here, the ingredient enclosure 440 includes a wall 442, creating a chamber 445. A launch tube 446 is disposed on one end of the chamber having fluid communication therewith. A pellet 448 is disposed in the launch chamber. A medicament 450 is positioned in the chamber 445. A power coil 444 is positioned around the launch tube 446. The ingredient enclosure 440 may have substantially composition as the ingredient enclosure 204, described with reference to FIG. 2A. The power coil 444 may be substantially similar to power coil 212 described with reference to FIG. 2A.

The launch tube 446 provides room for acceleration of the pellet 448, thus allowing for a better transfer of force to the medicament 450 and the cap (not shown). The pellet 448 is accelerated from an origination point to the opening of the chamber 445, using the magnetic force of the power coil 444, as described previously. The pellet 448 expels the medicament 450 on activation and acceleration. Since the medicament 450 is a solid dispersion, the pellet 448 is able to directly transfer force and thus expel the medicament 450.

Figure 4D:
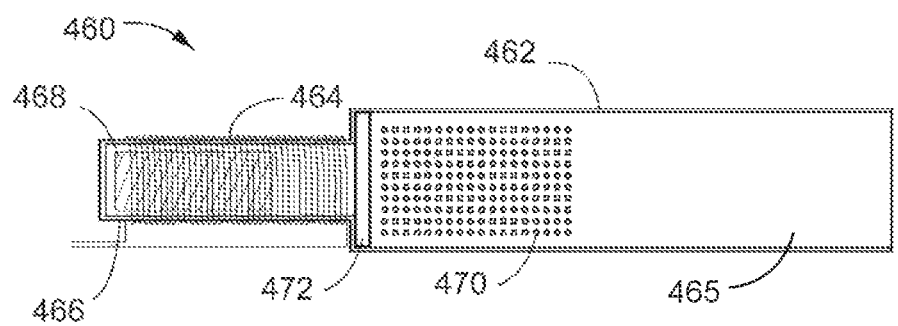

FIG. 4D depicts an ingredient enclosure 460 having a launch tube 466, according to another embodiment. As shown here, the ingredient enclosure 460 includes a wall 462, creating a chamber 465. A launch tube 466 is disposed on one end of the chamber. A pellet 468 is disposed in the launch tube 466. A medicament 470 is positioned in the chamber 465 with a seal 472 separating the medicament 470 from the launch tube 466. A power coil 464 is positioned around the launch tube 466. The ingredient enclosure 460 may have similar composition as the ingredient enclosure 204, described with reference to FIG. 2A. The power coil 464 may be substantially similar to power coil 212 described with reference to FIG. 2A.

The pellet 468 is accelerated from an origination point to the opening of the chamber 465, using the magnetic force of the power coil 464, as described previously. The pellet 468 can then transfer force to the seal 472. The seal 472 is then propelled forward to expel the medicament 470 and remove the cap. The seal 472 is fluidly sealed with the wall, through the use of a gasket and/or guide (not shown). Thus, the seal 472 provides a syringe like motion expelling the liquid medicament 470.

Figure 5:
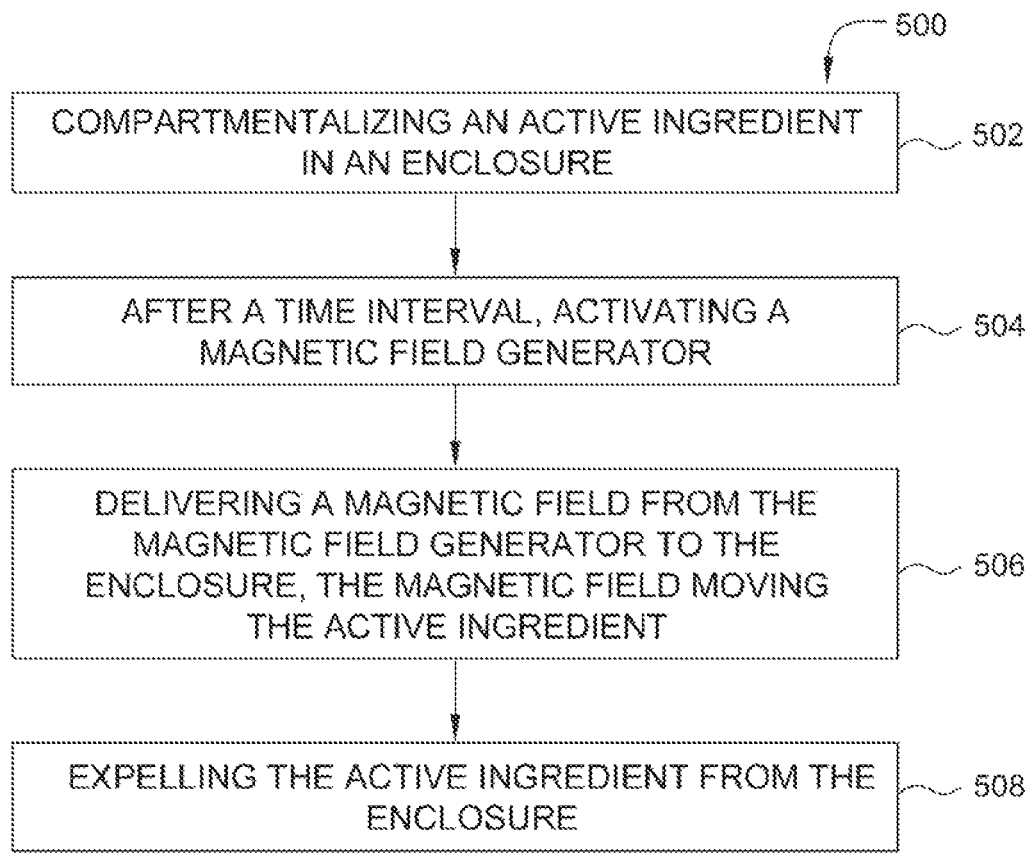
FIG. 5 is a block diagram of a method of delivering an active ingredient, according to embodiments described herein.

FIG. 5 is a block diagram of a method 500 of delivering an active ingredient, according to embodiments described herein. The method 500 includes compartmentalizing an active ingredient in an enclosure, at 502; after a time interval, activating a magnetic field generator, at 504; delivering a magnetic field from the magnetic field generator to the enclosure, the magnetic field moving a ferromagnetic pellet, at 506; and expelling the active ingredient from the enclosure, at 508. By controlling release of an active ingredient using a magnetic field, a dose of an active ingredient can be delivered at a specific time or at multiple specific times. This allows for easy dose administration and increases compliance with the dosing schedule designated by a clinician. Further, the use of magnetic fields allows for a completely sealed container. This reduces complexity of design and reduces the device failure rate.

The method 500 begins with compartmentalizing an active ingredient in an enclosure, at 502. The enclosure can be substantially similar in design and composition to the ingredient enclosure 204, described with reference to FIG. 2A. The enclosure can be sealed, such as by having sealed walls coming together to form an opening. A cap can then be positioned in the opening, creating a breakable seal. The enclosure can further include an active ingredient. The active ingredient may be selected from possible active ingredients described herein or others. Further, the enclosure or components therein can be configured to respond to a magnetic field, such as through the use of a ferromagnetic pellet or through the use of ferromagnetic colloidal dispersion with the active ingredient.

After a time interval, a magnetic field generator can be activated, at 504. The magnetic field generator can be any device capable of delivering a magnetic field to the enclosure, such that the active ingredients or other components are moved toward the opening of the enclosure. In one embodiment, the magnetic field generator is a power coil and a power source, as described above. The magnetic field generator is positioned such that the magnetic field is delivered to the enclosure. The magnetic field generator can be activated based on a programmed parameter, such as time, location, or a specific event. In one embodiment, the magnetic field generator is activated upon receiving a magnetic field. In another embodiment the magnetic field generator is activated upon entering the rumen of an animal, such as based on maintenance of a specific temperature.

The magnetic field can then be delivered from the magnetic field generator to the enclosure, at 506. The generated magnetic field is then delivered to the component which is configured to respond to a magnetic field. In embodiments using a ferromagnetic pellet, the ferromagnetic pellet is propelled toward the active ingredient. Thus, the magnetic field moves the active ingredient towards the opening of the enclosure. The active ingredient is then expelled from the enclosure, at 508. The magnetic field delivers the active ingredient and the pellet to the opening and the cap. The pressure from the active ingredient and the pellet dislodge the cap, thus breaking the seal on the enclosure. The active ingredients then are expelled into the rumen. One or more weights, as described above, may also be expelled with the active ingredient. Thus, the magnetic field is used to deliver the active ingredient in a time dependent and dose dependent fashion. Thus, the method described herein reduces error and unintentional non-compliance.

Figure 6:
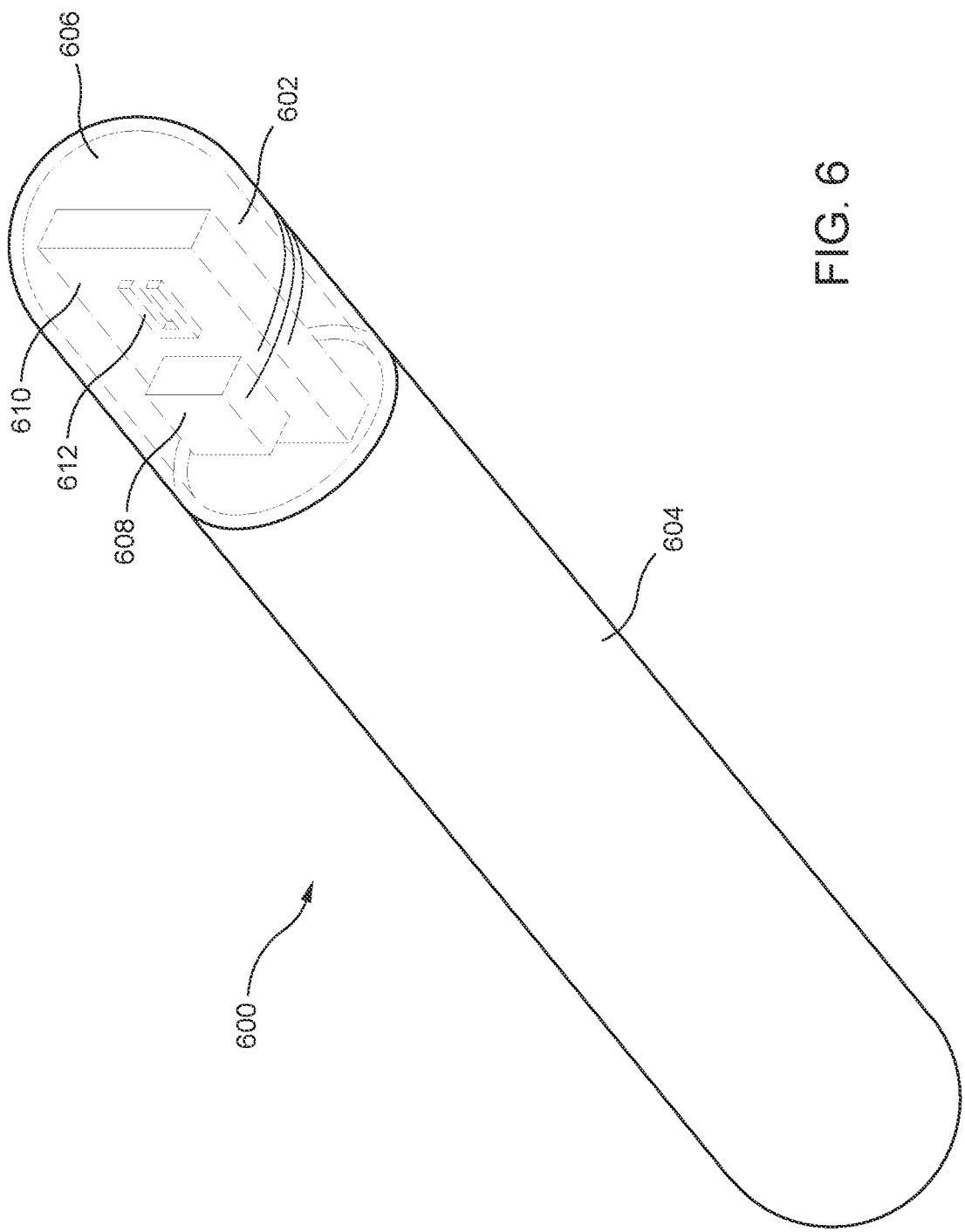
FIG. 6 is a side perspective view of an animal management device, according to embodiments described herein.

FIG. 6 is a side perspective view of an animal management device 600, according to embodiments described herein. The animal management device 600 includes an electronics portion 602, a base portion 604, and a cap 606. Collectively, the base portion 604 and the cap 606 define an interior region for housing the electronics portion 602.

The base portion 604 may comprise a metal, a magnetized material, or a permanent magnet. The base portion 604 may be used to collect foreign metal from an animal and reduce or eliminate metal disease. In addition, the base portion 604 may be used as a weight to keep the animal management device 600 within the animal. The base portion 604 may comprise more than fifty percent of the animal management device 600 to provide weight such that the animal management device 600 remains in the animal.

The outer dimensions of the animal management device 600 are, for example, about 4 inches in length and about 0.75 inches in diameter. The size of the animal management device 600 may be dictated by the size of the animal in which it will be inserted. The above embodiments are exemplary and not intended to be limiting of possible sizes. The outer dimensions of the animal management device 600 may be any dimensions at which the device may be safely inserted into an animal.

The electronics portion 602 includes a short range transceiver 608 run together with a computer processing unit (CPU) with memory 610 to store animal management information and a small antenna 612 to transmit animal management information. Examples of stored information include, but are not limited to, an identification number for an animal, vaccination schedules and unique disease information. The electronics portion 602 further includes a battery (not pictured). The CPU and memory 610 may additionally run an application code, which executes the described operations. The application code may also be run on a mobile device or computer to manage communications with the animal management device and provide updates to the animal management device remotely.

In operation, the electronics portion 602 is used to communicate the stored information with an external device, such as a mobile device, tablet, or computer. For example, the electronics portion 602 includes a radio device used to communicate location information of a specific animal, or multiple animals in a range, to a user. The user may dynamically change the range or view a strength indicator as the user roams the field. A communication range of the radio device may be adjusted from about 3 feet to about 50 feet or more. The received signal strength in the animal management device 600 is proportional to the distance between the user and the animal management device 600, such that the distance between the user and the animal management device 600 may be calculated to determine the rough location of the animal.

The electronics portion 602 may further include a global positioning system (GPS) device to provide location information of the animal, which is used to determine location information at intermittent or regularly scheduled intervals, such as twice daily, which is then stored in the electronics portion 602. In operation, the animal management device 600 will be in sleep mode and only wake up at intervals set by the user to preserve battery life. The intervals may, for example, be based on the activity of the animal or predetermined set time intervals. The battery is designed to last the lifetime of the animal, with the intervals set by the user being taken into consideration.

After data has been stored in the electronics portion 602, the user may download or synchronize the data with a cloud or local computer-based animal management database using Bluetooth technology, Wi-Fi technology or any other wireless communication method. The stored information may then be accessed by the user anywhere. For example, the user may access stored tracking information on a map for analysis.

The above described animal management device 600 may be used to permanently store animal management information, such as location and vaccine information, over the lifetime of the animal in a cost efficient and animal-friendly manner. Since the animal management device 600 may store a unique animal identification number, stolen animals may be identified and returned to their rightful owner. As an additional benefit, the animal management device 600 may reduce or eliminate the need for brand inspectors and ultimately may eliminate the need for branding altogether.

As described above in the descriptions of FIGS. 1 and 2, the animal management device 600, or portions thereof, may be combined with or incorporated into any of the devices described herein, such as devices 100, 200, 304, 324, and 344, to allow the devices to have both medicine delivery and animal management information storage capabilities. For example, portions of the animal management device, such as the electronics portion, may be incorporated into the electronic control device 106 or 206 such that the device 100 or 200 functions as a medicine delivery system and stores animal management information simultaneously.

Figure 7:
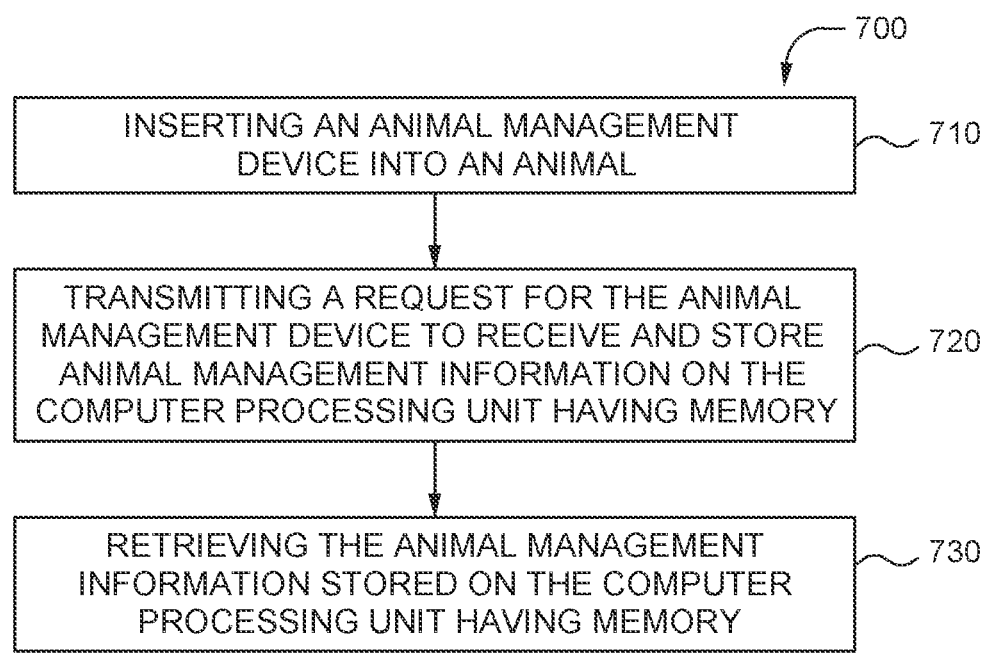
FIG. 7 is a block diagram of a method of animal management according to embodiments described herein.

FIG. 7 is a block diagram of a method 700 of animal management, according to embodiments described herein. At operation 710, the animal management device 600 is inserted into an animal. Insertion into the animal is facilitated by the size of the animal management device. Prior to operation 710, the animal management device 600 may be programmed to store animal management information at intermittent or predetermined time intervals. At operation 720, a signal is transmitted from a user to the animal management device 600. For example, the signal may include instruction to provide animal management information, such as location information, on demand or at predetermined intervals. The signal is received by the short range transceiver 608. Once the animal management information is attained by the animal management device 600, the animal management information may be stored in the electronics portion 602. At operation 730, a user receives the animal management information which has been stored by the animal management device 600.

Figure 8B:
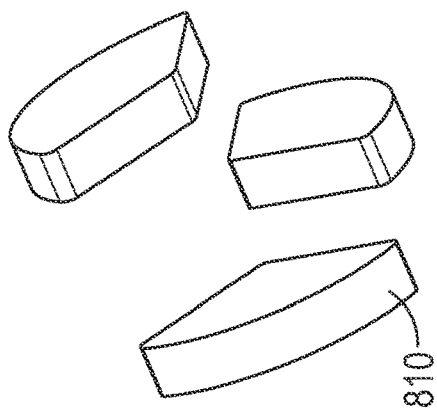
Figure 8B:
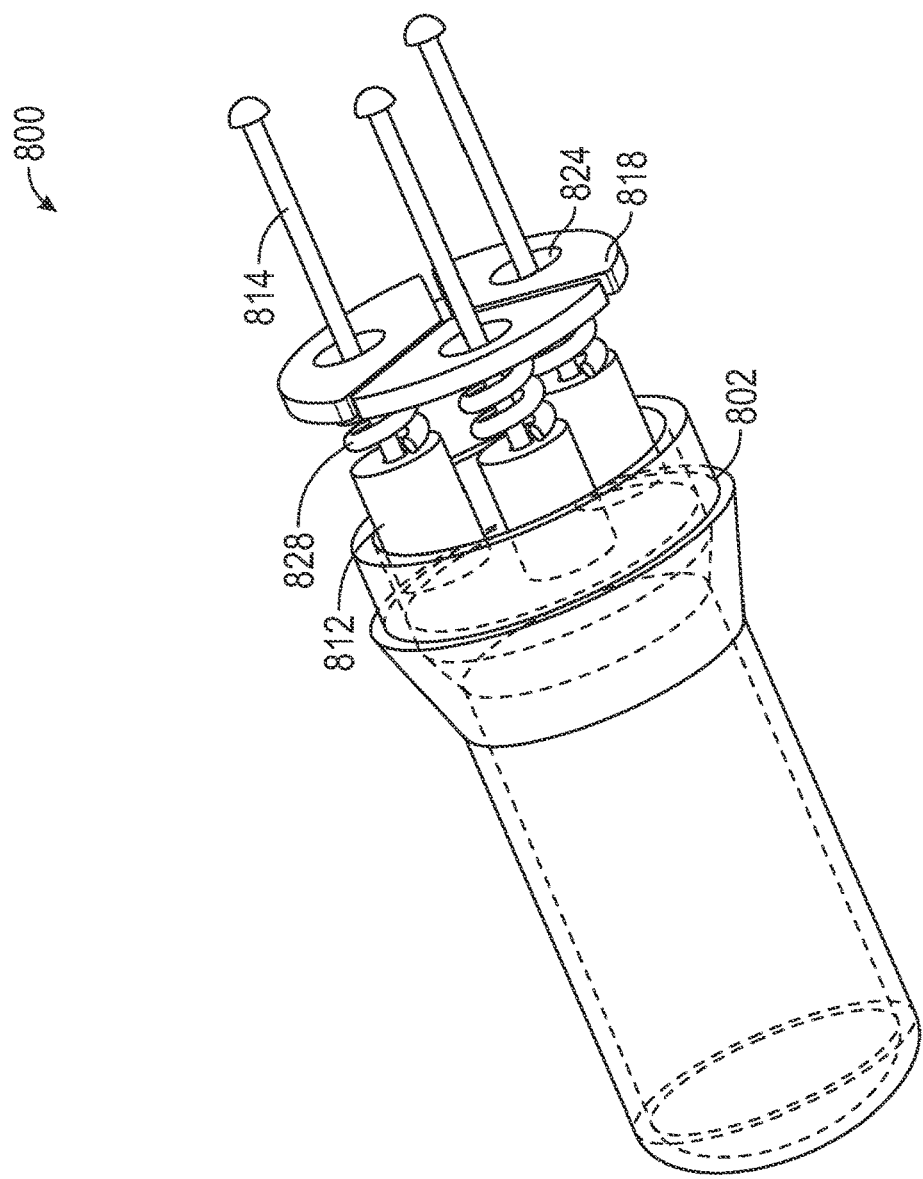
Figure 8C:
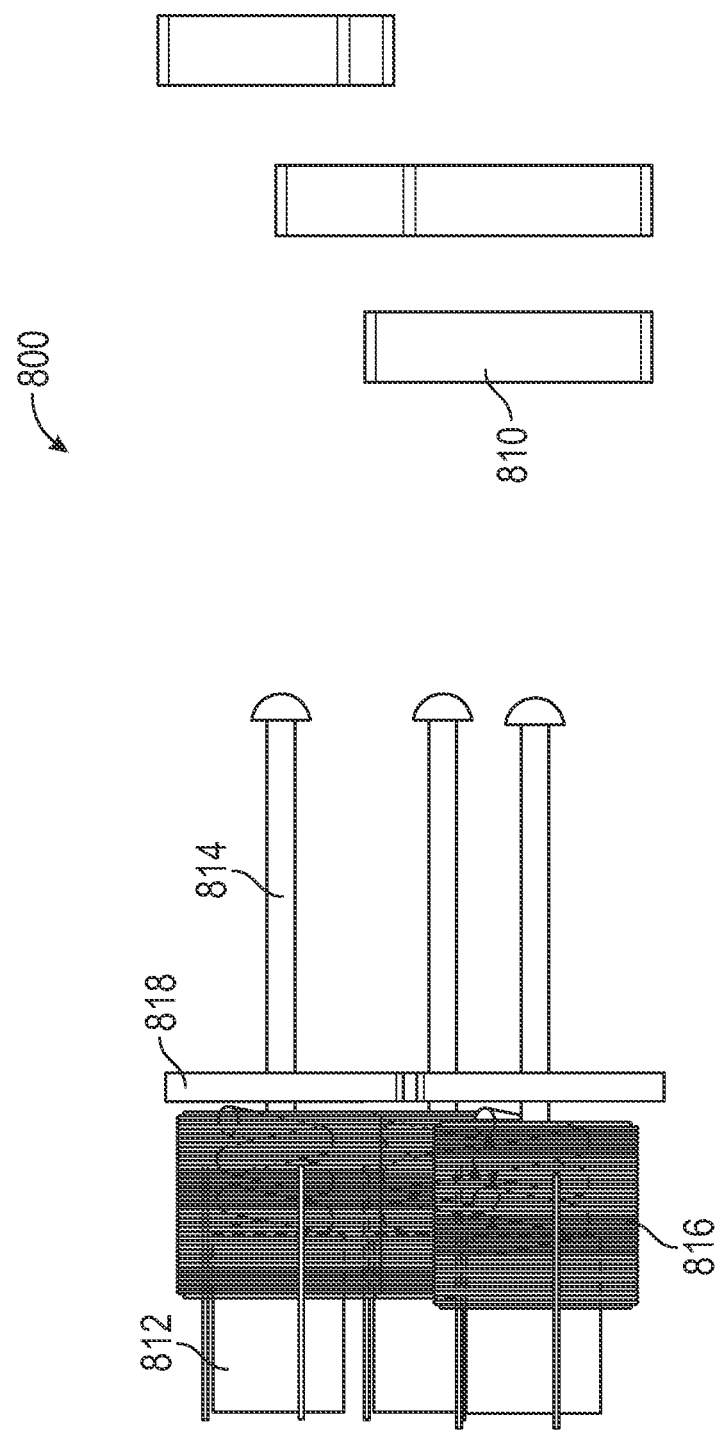
Figure 8D:
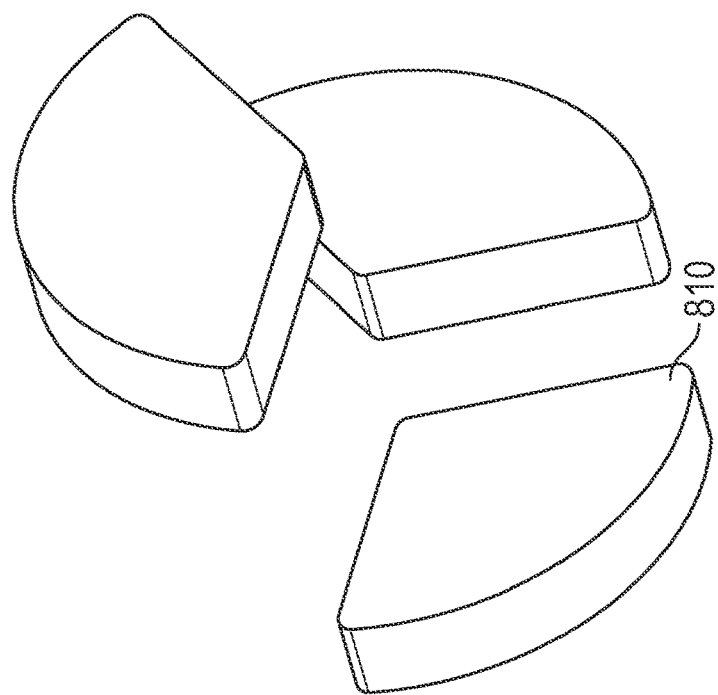
Figure 8D:
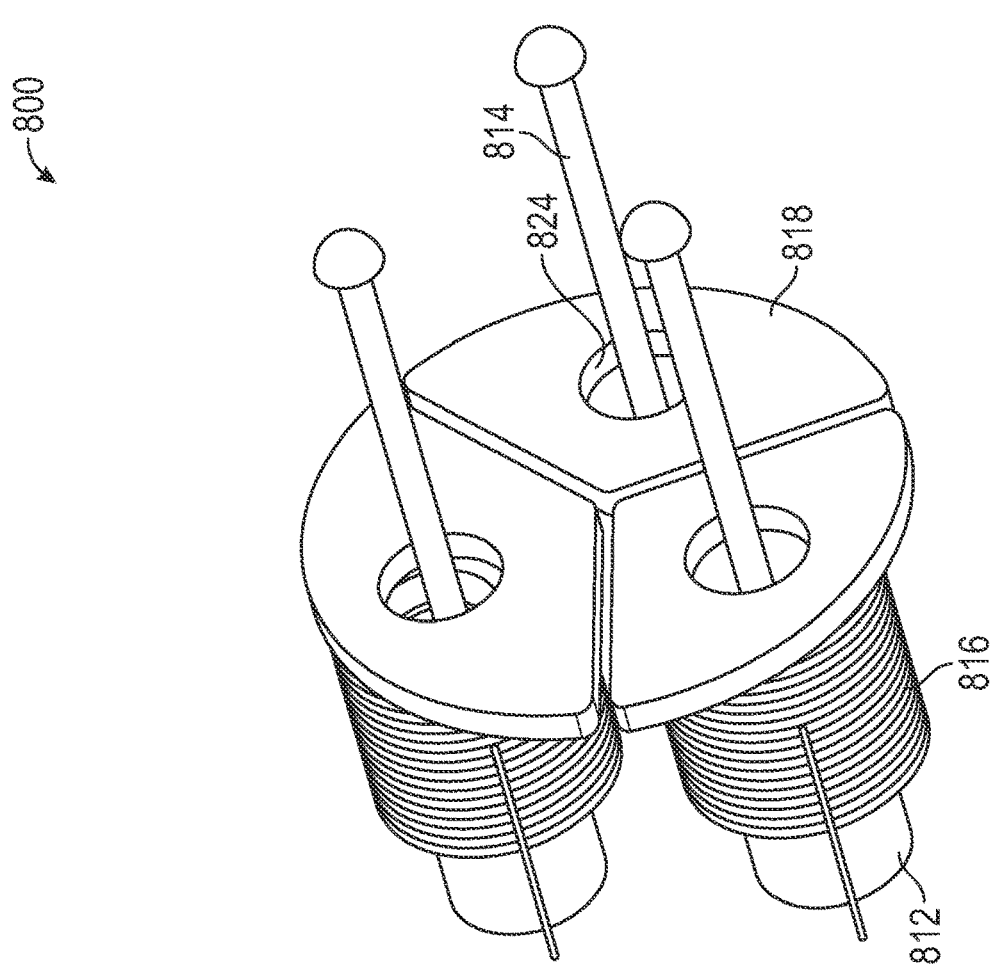
Figure 9A:
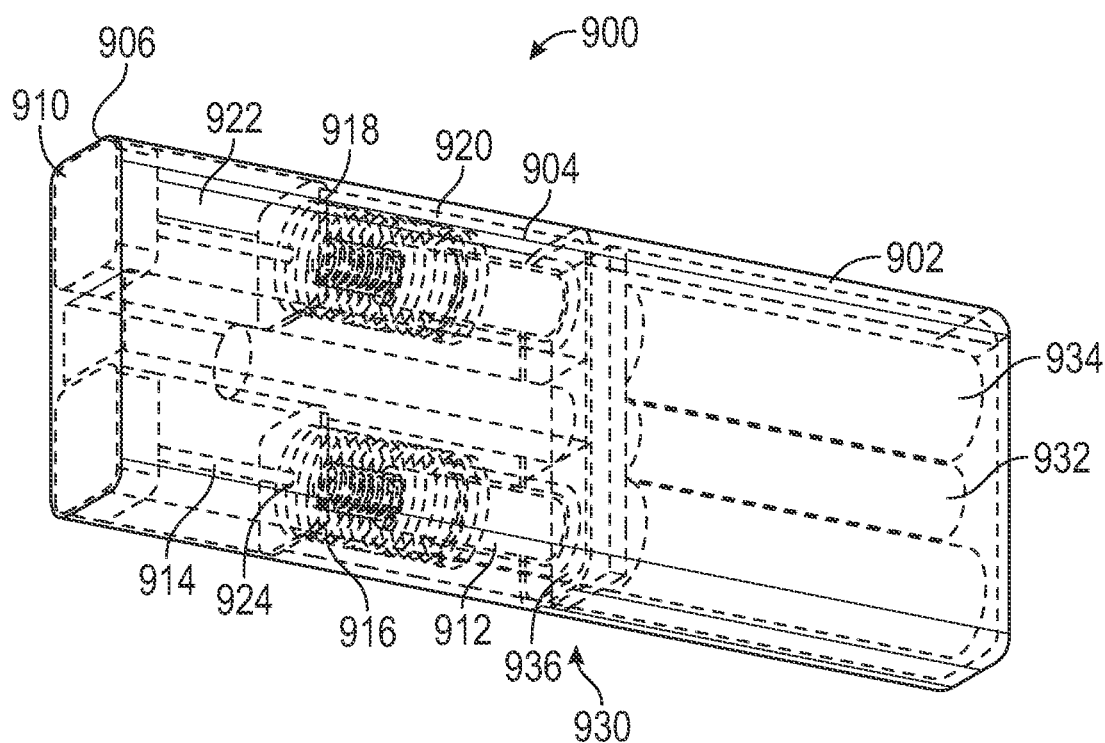
FIGS. 9A-9D are side views depicting a delayed delivery device, according to embodiments described herein.
Figure 9B:
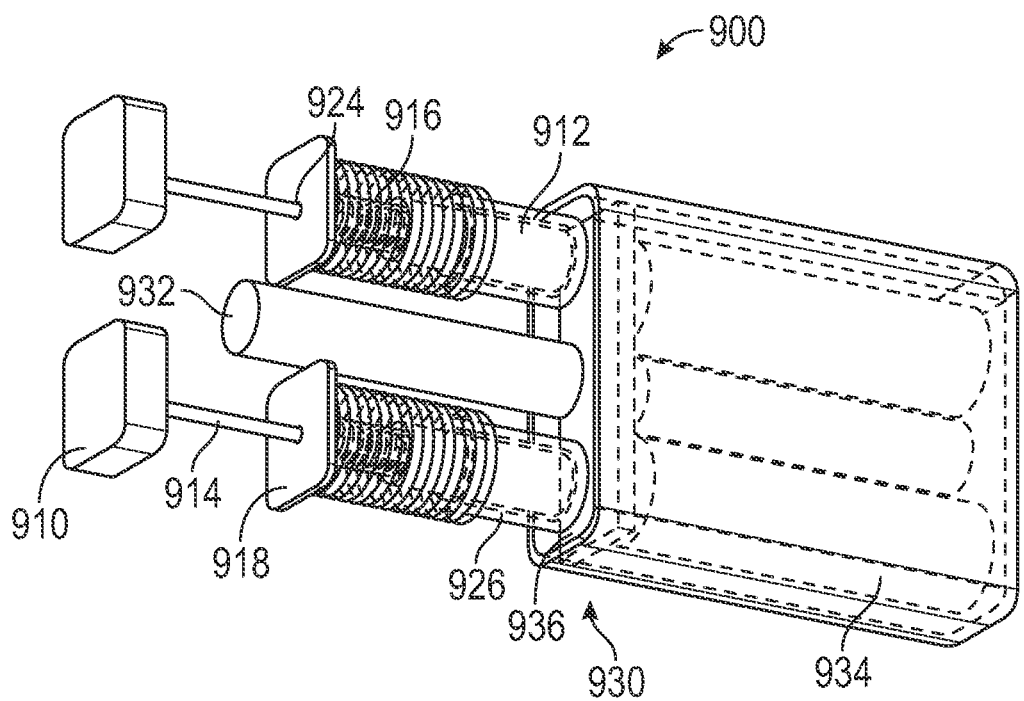
Figure 9C:
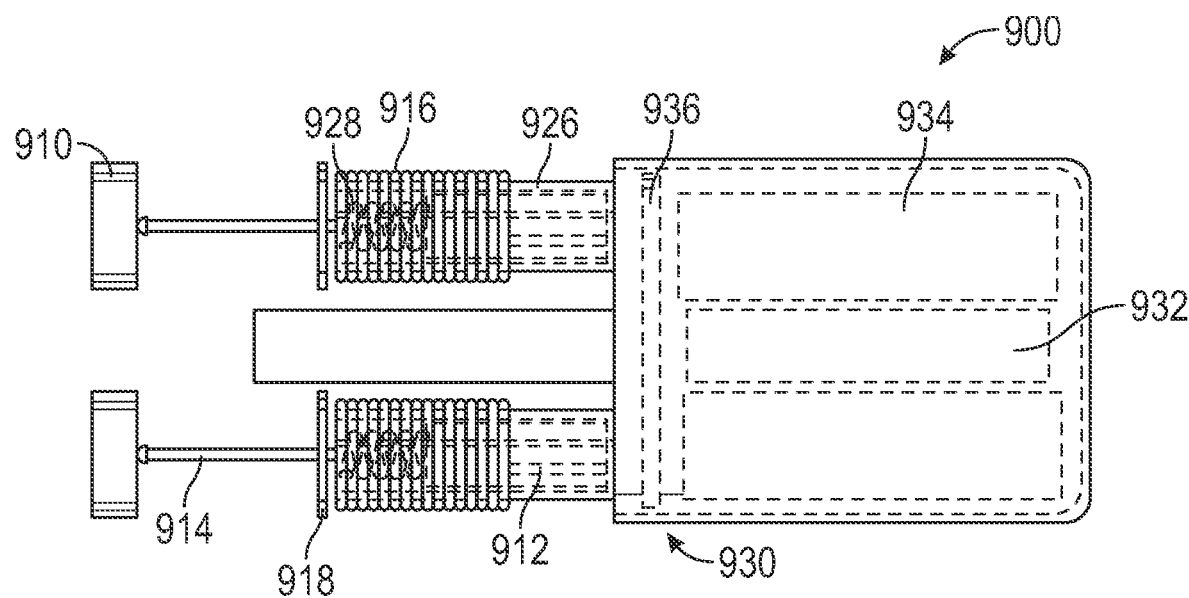
Figure 9D:
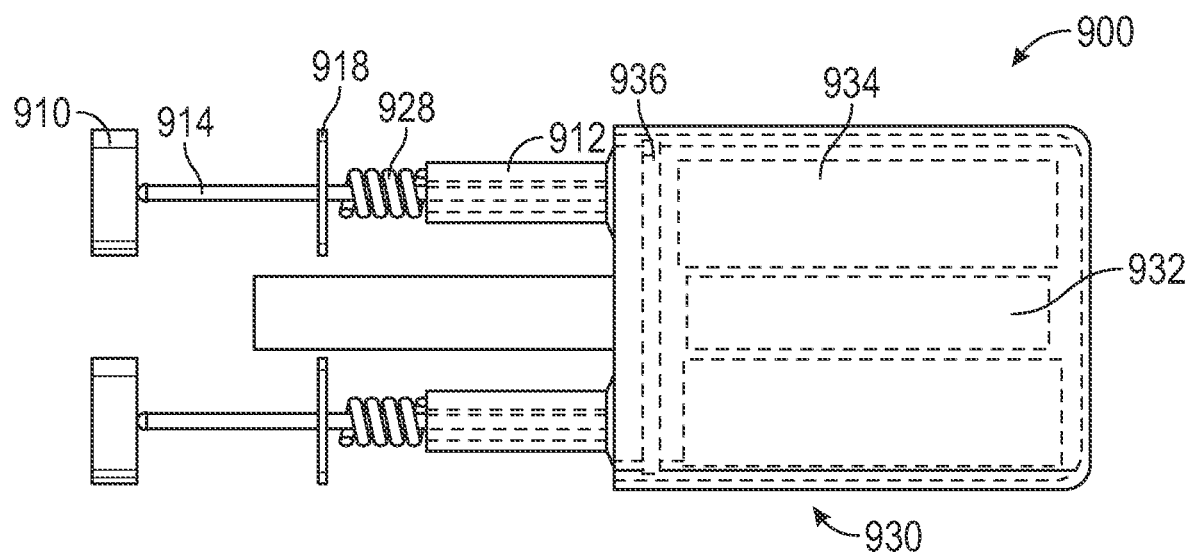

An alternative method of animal management may include programming the animal management device 600 to store animal management information, inserting the animal management device 600 into an animal, and transmitting a request to the animal management device 600 for the stored animal management information. The programming of the animal management device 600 may be modified to store or transmit various animal management information at intermittent or predetermined intervals FIGS. 8A-8D are multiple views of a delayed delivery device 800 for delivering an ingredient to an animal according to embodiments described herein. FIG. 8A shows a side perspective view of the delayed delivery device 800, and FIGS. 8B-8D show side perspective views of internal components of the delayed delivery device 800. The delayed delivery device 800 includes an enclosure 802, such as an ingredient disclosure, that defines an interior region 804 and a delivery opening 806. In particular, the enclosure 802 includes one or more walls 808 or partitions formed therein to define multiple interior regions 804, each having a delivery opening 806.

As the device 800 is used to deliver medicine or active ingredient(s), the active ingredient is inserted and contained within the interior regions 804, and later dispensed from the interior regions 804 through the delivery openings 806. As discussed above, the active ingredient may be in liquid form and/or granular or pellet form. The interior regions 804 are shown as having substantially the same size and shape as each other in this embodiment, but the present disclosure is not so limited. For example, the interior regions 804 may have different sizes with respect to each other, such as to deliver different amounts or types of active ingredients from each interior region 804.

A cap 810 (e.g., a stopper) is removably inserted or positioned into each of the delivery openings 806 to seal the delivery openings 806 and contain the active ingredient within each of the interior regions 804. The cap 810 is removable from the delivery opening 806, such as through movement of a pellet 812 to deliver the active ingredient from the interior region 804 through the delivery opening 806. A pellet 812, which includes or is formed from a ferromagnetic material, is movably positioned within each interior region 804 of the enclosure 802. Further, in this embodiment, an engagement member 814, such as a rod as shown, is positioned between the pellet 812 and the cap 810 within each interior region 804. The engagement member 814 is used to move and engage the cap 810 when the pellet 812 moves within the interior region 804. As the engagement member 814 engages the cap 810, the engagement member 814 pushes the cap 810 from the delivery opening 806, thereby enabling the active ingredient contained in the interior region 804 to be delivered from the enclosure 804 and into an animal.

As with the above embodiments, the delayed delivery device 800 may utilize a magnetic field to move and drive the pellets 812 within the enclosure 802. For example, a power coil 816 is included in the device 800 for each pellet 812 to move and drive the pellets 812 in the respective interior regions 804. The power coils 816 are electrically connected to an electronic control device (discussed more below) that includes a power source to selectively and independently provide power from the power source to the power coils 816. As power is provided to each power coil 816, the power coil 816 generates a magnetic field that interacts with the pellet 812 to move the pellet 812 in the device 800. As the pellet 812 then moves within the device 800, the pellet 812 moves the respective engagement member 814 to engage the cap 810.

Referring still to FIGS. 8A-8D, the delayed delivery device 800 includes a base plate 818 positioned in each interior region 804, such as to define a pellet chamber 820 and an ingredient chamber 822 within the interior region 804. The pellet 812 is movably positioned in the pellet chamber 820 with the active ingredient positioned within the ingredient chamber 822. Further, in an embodiment in which the pellet chamber 820 is not sealed from the ingredient chamber 822, the active ingredient may also be contained or flow at least partially into the pellet chamber 820.

The base plate 818, as shown, includes an aperture 824 formed therethrough, such as formed in a center of the base plate 818. The engagement member 814 extends through the aperture 824 between the pellet chamber 820 and the ingredient chamber 822. The engagement member 814 is used to engage a center of the cap 810, and the aperture 824 may be used to support and direct the engagement member 814 to engage the center of the cap 810. Further, though not shown here, the cap 810 may include a tapered edge in one or more embodiments. For example, the edge of the cap 810 that engages the enclosure 802 when inserted into the delivery opening 806 may be tapered. This may facilitate removal and ejection of the cap 810 from the delivery opening 806 when the engagement member 814 engages the cap 810, particularly if the cap 810 is able to deform when the engagement member 814 engages the cap 810. The cap 810 may include or be formed from an elastomeric material (e.g., rubber), in which the cap 810 may elastically deform when engaged by the engagement member 814 to facilitate removal of the cap 810 from the delivery opening 806.

In this embodiment, the enclosure 802 includes a launch tube 826 for each corresponding pellet 812. The launch tube 826 includes or has a cross-sectional shape corresponding to or complementing the cross-sectional shape of the pellet 812 to facilitate movement and direction of the pellet 812 within the launch tube 826. Thus, the launch tube 826 and the pellet 812 are not limited only to a circular cross-sectional shape, as shown in the present application. The launch tube 826 is shown positioned in the interior region 804, and more specifically within the pellet chamber 820, with the pellet 812 movably positioned within the launch tube 826. The power coil 816 is then positioned about or within the interior region 804, and more specifically positioned about or within the launch tube 826, for the magnetic field from the power coil 816 to interact with the pellet 812.

The engagement member 814 is shown as connected to the pellet 812 for the engagement member 814 to move with the pellet 812. Alternatively, the engagement member 814 may only be positioned between the pellet 812 and the cap 810 such that, when the pellet 812 moves, the pellet 812 engages the engagement member 814 (e.g., engages a base of the engagement member 814), with the engagement 814 moving to engage the cap 810.

In one or more embodiments, a biasing mechanism 828 may be included within the delayed delivery device 800, such as to apply a biasing force against the pellet 812. The biasing mechanism 828 is shown as positioned within the interior region 804, and more particularly within the launch tube 826, between the pellet 812 and the base plate 818. In an embodiment in which the biasing mechanism 828 includes a spring, as shown, the biasing mechanism 828 may be positioned about the engagement member 814 with the engagement member 814 extending through the biasing mechanism 828. The pellet 812 is movable between an initial position and an engaged position. In this embodiment, in the initial position, the pellet 812 is shown at a distal end of the launch tube 826 with respect to the delivery opening 806, and in the engaged position, the pellet 812 moves towards a proximal end of the launch tube 826 with respect to the delivery opening 806 for the engagement member 814 to engage the cap 810. The power coil 816 is used to move the pellet 812 from the initial position to the engaged position, and the biasing mechanism 828 is used to move the pellet 812 from the engaged position to the initial position. If the pellet 812 is moved towards the engaged position and is not able to remove the cap 810 from the delivery opening 806, the biasing mechanism 828 is able to move the pellet 812 back towards the initial position to re-attempt to remove or dislodge the cap 810 from the delivery opening 806.

As discussed above, a delayed delivery device in accordance with embodiments disclosed herein may be used to deliver a medicine or active ingredient to the stomach of an animal, such as a ruminant animal. However, the present application is not so limited, as a delayed delivery device may be used in other types of animals, such as non-ruminant animals, and may be used to deliver an active ingredient to other portions of an animal, such as under the skin of the animal (e.g., subcutaneous). Accordingly, FIGS. 9A-9D are multiple views of a delayed delivery device 900 for delivering an ingredient, such as subcutaneously, to an animal according to embodiments described herein. Further, though the present application is not so limited, for perspective the delayed delivery device 900 shown in FIGS. 9A-9D is 5 in (12.7 cm) in length and 0.5 in (1.3 cm) in thickness.

As with the above embodiments, particularly the delayed delivery device 800, the delayed delivery device 900 includes an enclosure 902 with multiple interior regions 904 and a cap 910 removably inserted into each delivery opening 906 of the enclosure 902. A base plate 918 is positioned in each interior region 904 to define a pellet chamber 920 and an ingredient chamber 922 with a pellet 912 positioned in the pellet chamber 920 and the ingredient chamber 922 used to contain the active ingredient. In particular, each pellet 912 is movably positioned within a launch tube 926 with a biasing mechanism 928 positioned within each launch tube 926 between the pellet 912 and the base plate 918. An engagement member 914 is coupled or connected to each pellet 912 with the engagement member 914 extending through an aperture 924 of the base plate 918 between the pellet 912 and the cap 910. A power coil 916 is positioned within the interior region 904 and about each pellet 912 to provide a magnetic field that will move the pellet 912 within the enclosure 902.

Further, as with the above embodiments, the delayed delivery device 900 includes an electronic control device 930 electrically connected to the power coils 916 to selectively and independently control the power coils 916, and thus selectively and independently control the pellets 912 corresponding to each of the power coils 916. The electronic control device 930, as shown, includes a power source, such as a battery 932 and/or a capacitor 934 corresponding to each power coil 916 or pellet 912. The electronic control device 930 further includes an electronics board 936, such as a printed circuit board, with the power coils 916 and the power source electrically connected to each other through the board 936. A processing unit that has memory (e.g., a storage chip, an SD memory, or a flash memory) may also be included with the electronic control device 930, such as on the electronics board 936. In addition, an antenna and/or other communications device or chip (e.g., a Bluetooth chip) may be included on or electrically connected to the electronics board 936 to enable wireless communication with the electronic control device 930.

In accordance with one or more embodiments, a delayed delivery device may include or be used with a sensor to measure a physiological parameter of an animal. For example, with reference to FIGS. 9A-9D, a sensor may be included within or operably coupled to the delayed delivery device 900. In such embodiments, the sensor is electrically connected to the electronic control device 930, such as through the electronics board 936, to control the sensor, to store the measured physiological parameters from the sensor (e.g., in the memory), and/or to communicate the measured physiological parameters (e.g., with the antenna).

The sensor may be used to measure a physiological parameter of the animal, which may include, but is not limited to, the pressure, temperature, conductivity, pH valve, and/or ammonia of the animal. In one embodiment, the sensor may be included within the enclosure 902 of the delayed delivery device 900 to be in fluid communication with the animal through the interior region 904 or the ingredient chamber 922. Alternatively, the sensor may be positioned within a separate sensor chamber within the enclosure 902 that is fluidly sealed from the interior region 904 or the ingredient chamber 922. The sensor chamber may then be in fluid communication (e.g., through a port or aperture formed through the enclosure 902) with an exterior of the enclosure 902 to measure the physiological parameter of the animal through the enclosure 902. As the delayed delivery device 900 may be embedded subcutaneously within the animal, as opposed to within a stomach of the animal, this may enable the sensor to more accurately measure the physiological parameter of the animal. Further, the subcutaneous location of the delayed delivery device 900 may facilitate communication with the delayed delivery device 900, as the antenna or communication device will be located closer to the surface of the animal.

A sensor is discussed above with respect to the subcutaneous embodiment in FIGS. 9A-9D, but the present disclosure is not so limited, as a sensor may be included within any embodiment of the present disclosure. In particular, a sensor may be included within a delayed delivery device used to be positioned within the stomach or rumen of an animal in accordance with the present disclosure, such as to measure the temperature of the animal.

In an embodiment in which a sensor is used to measure a temperature of an animal, such as in a stomach or rumen embodiment, a subcutaneous embodiment, or any other embodiment in accordance with the present disclosure, the sensor may be fluidly sealed from fluids or interaction with the animal. For example, the sensor may be positioned and/or fluidly sealed within the delayed delivery device. However, the sensor may be thermally coupled with fluids or interaction with the animal, such as through the use of a thermally conductive material included within the delayed delivery device. A thermally conductive material, such as a thermally conductive plastic or a material having thermally conductive fibers (e.g., metal) positioned therein, may be used to facilitate thermal conduction and communication between an exterior and an interior of the delayed delivery device. The thermally conductive material, which may have a lower thermal resistivity compared to other materials used within the enclosure of the delayed delivery device, would be in direct contact or communication with fluids or another portion of the animal. The sensor may then be in direct contact or communication with the thermally conductive material such that the temperature of the animal is communicated to the sensor through the thermally conductive material. Thus, by measuring the temperature of thermally conductive material, the sensor may be able to measure the temperature of the animal while being fluidly sealed from fluids or interaction with the animal but still being thermally coupled to or in communication with the animal.

Figure 10:
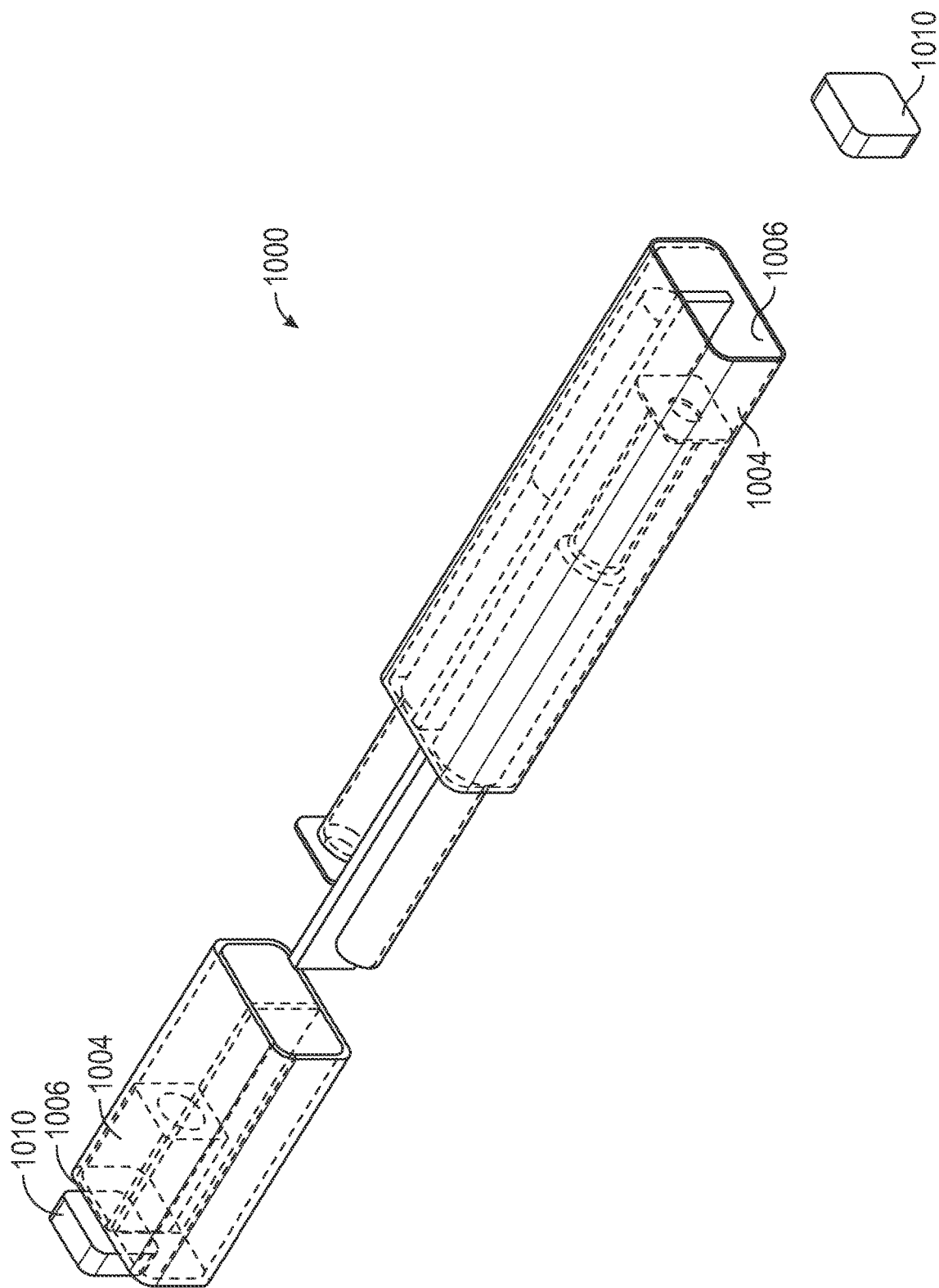
FIG. 10 is side view depicting a delayed delivery device, according to embodiments described herein.

Referring now to FIG. 10, a side view of a delayed delivery system 1000 according to embodiments described herein is shown. The delayed delivery system 1000 may be similar to the delayed delivery system 900. However, in this embodiment, the caps 1010, delivery openings 1006, and interior regions 1004 are oriented in opposite directions with respect to each other, thereby enabling an active ingredient contained within the interior regions 1004 to be delivered in opposite directions with respect to each other. For example, in the embodiment shown in FIGS. 9A-9D, as the caps 910, delivery openings 906, and interior regions 904 are oriented in the same direction with respect to each other, gravity will similarly affect (e.g., assist or work against) the delivery of the active ingredient from the delayed delivery system 900. Alternatively, in the embodiment in FIG. 10, gravity will oppositely affect the delivery of the active ingredient from one delivery opening 1006 with respect to the other from the delayed delivery system 1000.

Figure 11A:
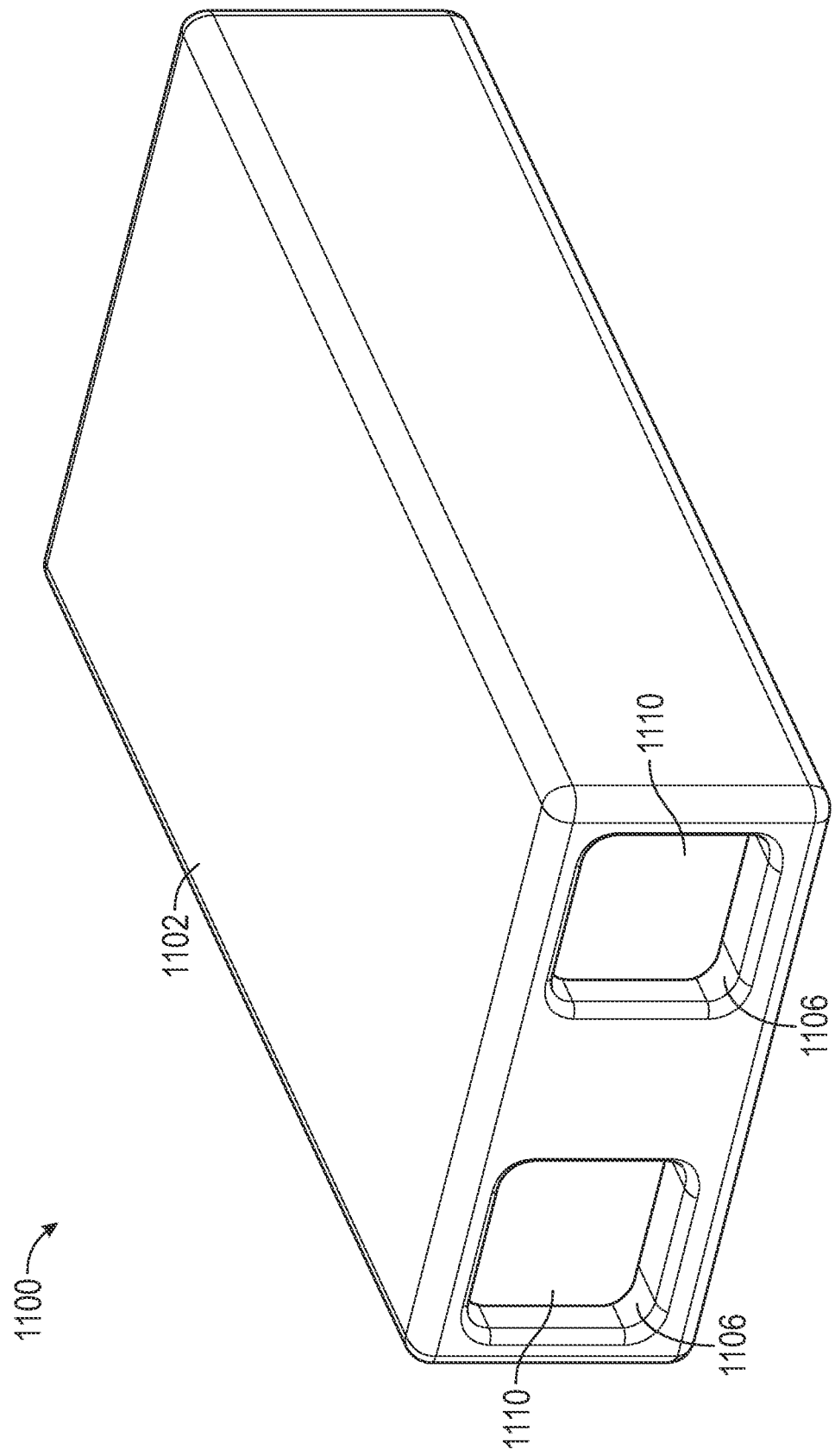
FIGS. 11A-11C are side views depicting a delayed delivery device, according to embodiments described herein.
Figure 11B:
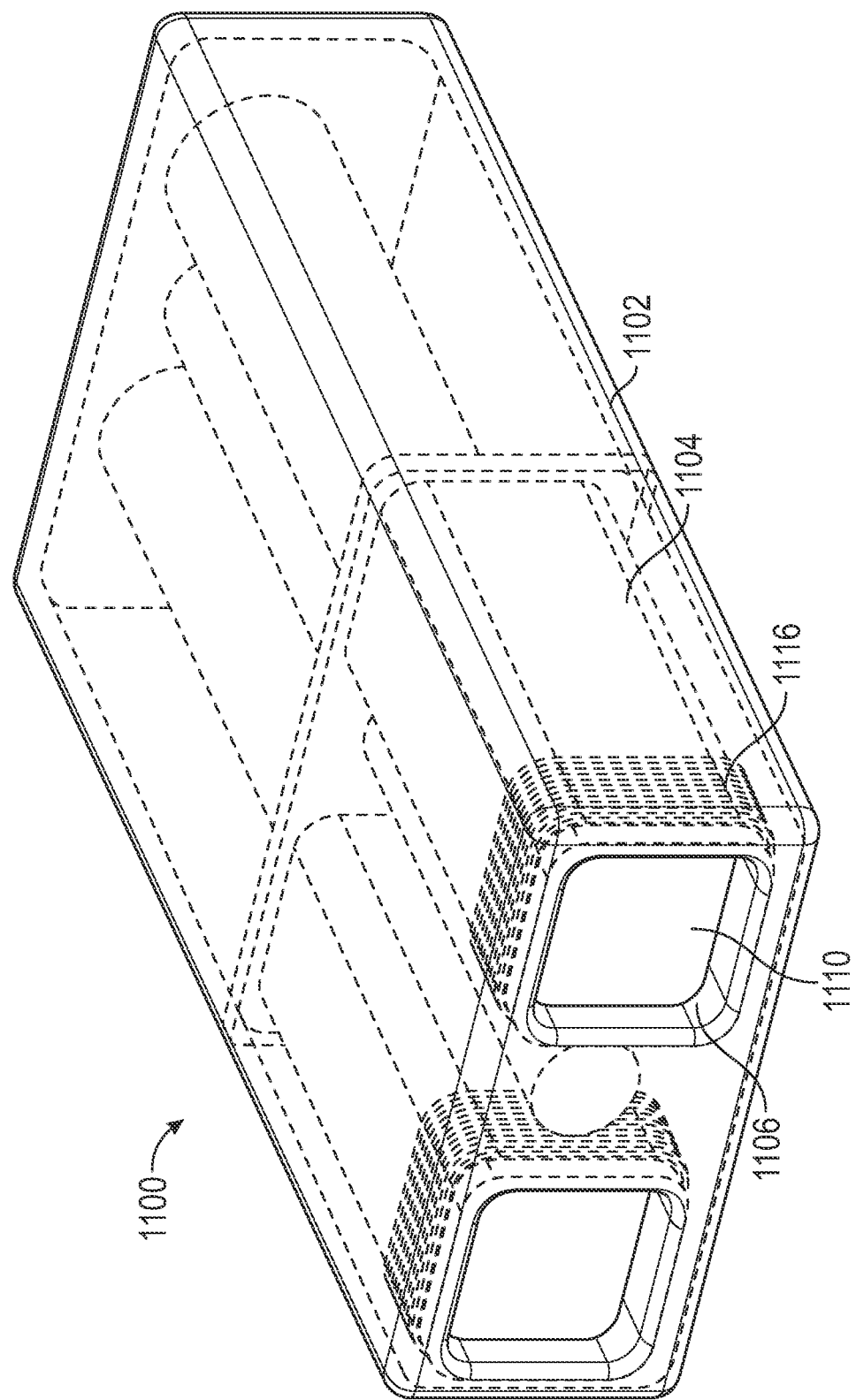
Figure 11C:
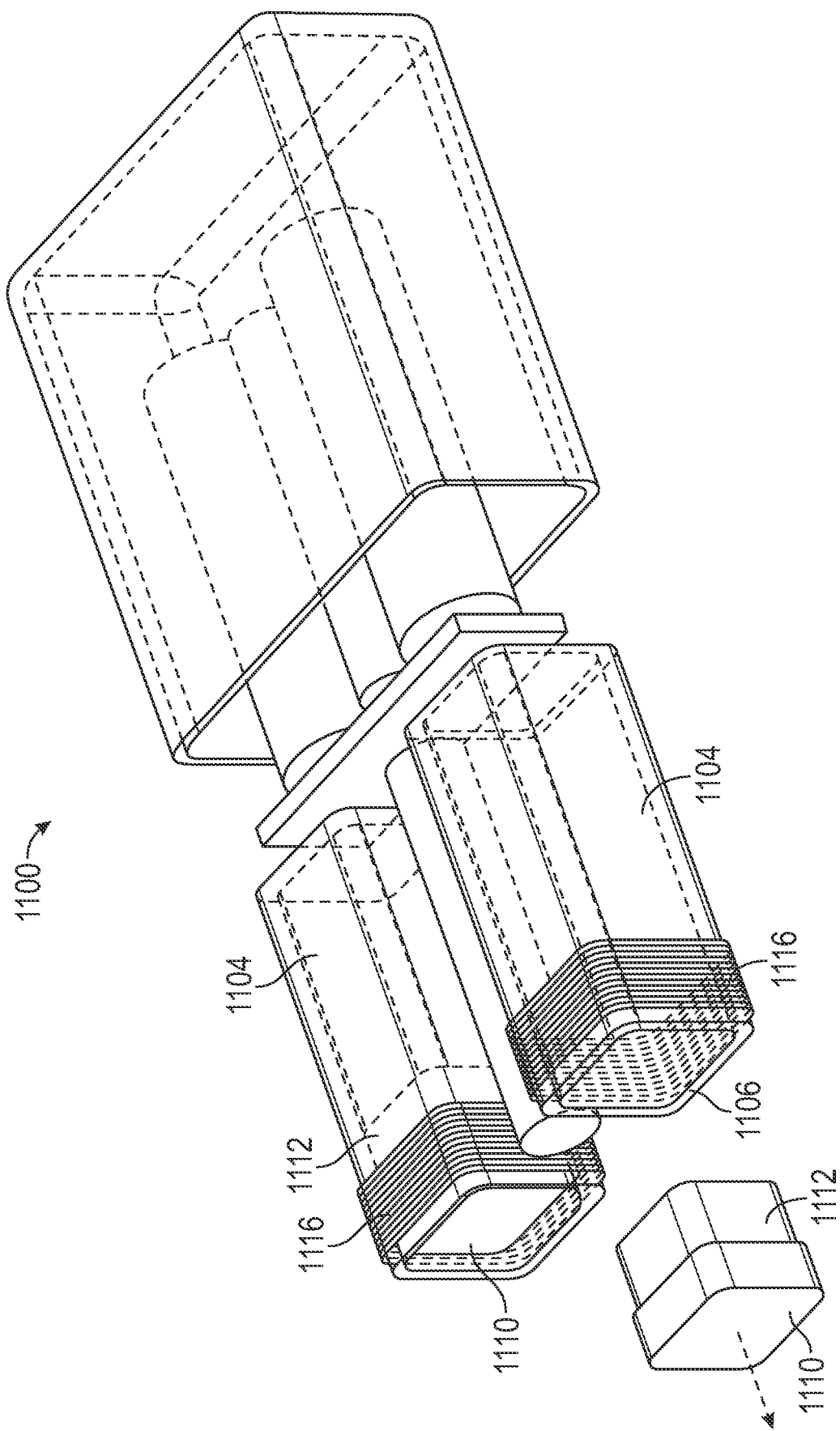

Referring now to FIGS. 11A-11C, multiple views of a delayed delivery device 1100 for delivering an ingredient to an animal according to embodiments described herein are shown. In the above embodiments, in particular with the delayed delivery device 800 and the delayed delivery device 900, an engagement member is used to engage a cap to remove the cap from a delivery opening of the delayed delivery device. However, the present disclosure is not so limited, and may include other embodiments that do not include an engagement member.

Accordingly, FIGS. 11A-11C show the delayed delivery device 1100, similar to the delayed delivery device 900, but without an engagement member in this embodiment. The delayed delivery device 1100 includes an enclosure 1102 with multiple interior regions 1104 and a cap 1110 removably inserted into each delivery opening 1106 of the enclosure 1102. A pellet 1112 is positioned within each interior region 1104 with the pellet 1112 connected to the cap 1110 and/or positioned directly adjacent to the cap 1110. For example, the pellet 1112 is connected to the cap 1110 in this embodiment such that the pellet 1112 and cap 1110 move together with respect to each other (e.g., are stationary or are not movable with respect to each other). However, in another embodiment, the pellet 1112 and the cap 1110 may be positioned directly adjacent to each other but movable with respect to each other. In such an embodiment, the pellet 1112 and the cap 1110 may or may not be tethered to each other.

A power coil 1116 associated with each pellet 1112 is positioned about or within the interior region 1104. The power coil 1116 at least partially overlaps with or is positioned about the pellet 1112 and/or the cap 1110. For example, as the pellet 1112 is shown as positioned at the proximal end of the interior region 1104 with respect to the delivery opening 1106, the power coil 1116 associated with each pellet 1112 is also positioned at the proximal end of the interior region 1104 with respect to the delivery opening 1106. When power is supplied to the power coil 1116, the power coil 1116 generates a magnetic field to interact with and move the pellet 1112. As the pellet 1112 is connected to and/or positioned directly adjacent the cap 1110 (e.g., without any active ingredient positioned between the pellet 1112 and the cap 1110), the pellet 1112 directly engages the cap 1110 to apply a force against the cap 1110. This enables the pellet 1112 to push and remove the cap 1110 from the delivery opening 1106, along with the pellet 1112, to deliver the active ingredient from the interior region 1104.

In accordance with one or more embodiments, a delayed delivery device may be used for providing multiple injections or scheduled vaccinations for an animal. For example, a first vaccination may be provided to an animal when a delayed delivery device is installed within an animal. The delayed delivery device may then be used to provide one or more additional injections or vaccinations to the animal at predetermined times or intervals. For tick control of an animal, two additional vaccinations are usually required with each vaccination requiring between 1 to 3 mL. Thus, the delayed delivery device, such as the delayed delivery devices 900 or 1100, may be used to provide the two additional vaccinations at separate instances. The first additional vaccination may be provided or delivered at a first predetermined interval (e.g., twenty-eight days later) after the initial vaccination, and the second additional vaccination may be provided or delivered at a second predetermined interval (e.g., six months later) after the initial vaccination or the first additional vaccination.

Further, in one or more embodiments multiple delayed delivery devices may be used within an animal. For example, a delayed delivery device in accordance with the present disclosure may be positioned within the stomach or rumen of an animal to deliver oral treatments, and another delayed delivery device in accordance with the present disclosure may be positioned subcutaneously within the animal to deliver injections or vaccinations. This may provide the advantage that an individual may rely on the delayed delivery devices to provide regularly scheduled treatments and vaccinations to the animal, with the individual then needing to only periodically (e.g., once a year) check the animals, such as to refill or change out the delayed delivery devices. In such an embodiment, the delayed delivery devices may be able to communicate with each other, such as for data storage and/or control of each other.

As discussed above, a delayed delivery device in accordance with the present disclosure may be used to collect and/or store data with respect to the animal that the device is positioned within. For example, a delayed delivery device may be used to collect location based data with respect to the animal, such as through the use of a GPS or similar tracking device included within the delayed delivery device, and/or may be used to collect physiological or health related data with respect to the animal, such as through the use of a sensor included within the delayed delivery device.

Further, the electronics portion or the electronic control device of the delayed delivery device may be able to store the data and/or communicate the data from the delayed delivery device. In one embodiment, the delayed delivery device is able to communicate wirelessly, such as using Bluetooth technology, Wi-Fi technology, cellular technology (e.g., through the use of a cellular network), or any other wireless technology or communication method. The subcutaneous embodiment of the delayed delivery device for instance, shown in FIGS. 9A-9D at least, advantageously may facilitate wireless communication with the delayed delivery device while also providing protection by being embedded underneath the skin of the animal. For example, by having the delayed delivery device embedded subcutaneously within the animal, the wireless antenna or electronics portion of the delayed delivery device will have less interference for communication, as compared to a delayed delivery device included within the stomach or rumen of an animal. This facilitates communication with and control of the delayed delivery device. However, the present disclosure contemplates using wireless communication with all embodiments in accordance with the present disclosure (such as installed subcutaneously or within the rumen of an animal), in which multiple or different wireless frequencies (Bluetooth, Wi-Fi, cellular, or otherwise) used to communicate with other electronics may be used within embodiments of the present disclosure. Further, by having the delayed delivery device embedded subcutaneously within the animal, this provides additional protection and containment for the delayed delivery device, as compared to a tracking device included externally on the animal. An ear tag, for example, may be included externally on an animal for tracking purposes. However, such an external tracking device may be lost or easily damaged, as compared to a subcutaneous delayed delivery device in accordance with the present disclosure, as the animal may even chew on or bite off the external tracking device (e.g., ear tag).

As discussed above, a user may download and access stored location based data or tracking information of one or more animals, such as on a map for analysis, in accordance with one or more embodiments of the present disclosure. For example, a cellular network may be used to communicate with the delayed delivery devices installed within one or more animals to receive the current and/or historical locations of each of the animals. The delayed delivery devices may each be able to save location based data for each animal, such as at predetermined time intervals (e.g., every 12 or 24 hours), in which this location based data for each animal may be retrieved wirelessly from the delayed delivery devices. This location based data may be overlaid on a map, for instance, to examine or optimize the location of the animals individually or collectively.

In one embodiment, it may be desired to create a barrier or wall with the animals, such as for purposes of pest control or containment, in which the location based data will facilitate such positioning of the animals. With respect to the pest control (e.g., for ticks) discussed above, the animals may be positioned to facilitate containment or spreading of the pests with respect to a predetermined area. An animal using a delayed delivery device in accordance with the present disclosure may be supplied with medicine or other active ingredient not only for immunization or treatment, but also to control or kill such pests when in proximity of such pests. Thus, knowing that an animal has a delayed delivery device in accordance with the present disclosure, the animal may be deployed or positioned within an area that has a high contamination of pests for the animal to attract the pests, and then subsequently control and kill such pests. When used in conjunction with additional animals also having delayed delivery devices, the animals may be used to create a barrier or virtual wall for the pest control by using selective positioning of the animals (e.g., along a property line to prevent contamination of pests across the property line). As such, the location based data received from the delayed delivery devices of such animals may be used to facilitate positioning of the animals or adding additional with respect to the desired pest control.

Described herein are devices for delayed delivery of an active ingredient. The devices include an electronic control which can power a power coil. The power coil provides a magnetic field to an ingredient enclosure such that the active ingredient can be expelled. The electronic control further includes a timer, such that medicine can be delivered at a distant period of time. Further, multiple ingredient enclosures can be used thus allowing for time controlled release of a full active ingredient regimen.

Also described herein are devices for storing animal management information, which may stand alone or may be combined with the devices for delayed delivery of an active ingredient. The devices include an electronics portion, a base portion, and a cap. The electronics portion includes a transceiver for sending and receiving animal management information, a CPU with memory for storing the animal management information, and an antenna. The base portion comprises a magnetic material for reducing metal disease and holding the animal management device in place in the animal. The devices may further include a battery, which is designed to last the lifetime of the animal and a GPS device, which may regularly or intermittently provide location information of the animal.

While the foregoing is directed to embodiments of the present disclosure, other and further embodiments of the disclosure may be devised without departing from the basic scope thereof, and the scope thereof is determined by the claims that follow.

What is claimed is:

1. A delayed ingredient delivery device, comprising:
    an ingredient enclosure defining an interior region and a delivery opening;
    a cap that seals the delivery opening;
    a pellet movably positioned in the interior region;
    a tether coupled to the pellet, the tether comprising a metallic material, the tether configured to retain the pellet; and
    an electronic control device comprising a power source, the electronic control device configured to move the pellet relative to the tether; and
    a power coil disposed around the ingredient enclosure, the power coil electrically connected with the power source to generate a magnetic field which interacts with the pellet in the interior region and moves the pellet through the interior region to displace the cap.

2. The device of claim 1, wherein the pellet comprises a ferromagnetic material.

3. The device of claim 2, wherein the ferromagnetic material is one of iron, nickel, cobalt, and alloys thereof.

4. The device of claim 1, wherein the power coil at least partially overlaps and is positioned around the pellet.

5. The device of claim 4, wherein the pellet is positioned at a distal end of the interior region opposite to the delivery opening.

6. The device of claim 1, wherein the power source is a battery.

7. The device of claim 6, wherein the electronic control device further comprises a capacitor and an electronics board.

8. The device of claim 1, wherein the electronic control device further comprises a wireless communication device to enable wireless communication with the electronic control device.

9. A delayed ingredient delivery device, comprising:
    an ingredient enclosure defining an interior region and a delivery opening;
    a cap to seal the delivery opening;
    a ferromagnetic pellet movably positioned in the interior region;
    a tether coupled to the ferromagnetic pellet, the tether comprising a metallic material, the tether configured to retain the pellet;
    an electronic control device comprising a power source, an electronics board, and an antenna for wireless communication, the electronic control device configured to move the ferromagnetic pellet; and
    a power coil disposed around the ingredient enclosure and electrically connected with the power source to generate a magnetic field which interacts with the ferromagnetic pellet in the interior region and moves the ferromagnetic pellet through the interior region to displace the cap, the ferromagnetic pellet configured to apply a force against the cap.

10. The device of claim 9, wherein the power source is a battery and the electronic control device further comprises a capacitor.

11. The device of claim 10, wherein the power coil wraps around at least a portion of the ferromagnetic pellet.

12. The device of claim 1, wherein the tether retains the ferromagnetic pellet within the enclosure opposite the cap.

13. The device of claim 10, wherein the tether retains the ferromagnetic pellet within the ingredient enclosure opposite the cap.

* * * * *